(12) United States Patent
Zhang et al.

(10) Patent No.: US 11,160,742 B2
(45) Date of Patent: Nov. 2, 2021

(54) METHODS AND COMPOSITIONS FOR IMPROVING HAIR COLOR FASTNESS AND REJUVENATING HAIR COLOR

(71) Applicant: L'Oreal, Paris (FR)

(72) Inventors: Guojin Zhang, Westfield, NJ (US); Ronak Rughani, Edison, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/715,079

(22) Filed: Dec. 16, 2019

(65) Prior Publication Data

US 2020/0197283 A1 Jun. 25, 2020

Related U.S. Application Data

(60) Provisional application No. 62/784,001, filed on Dec. 21, 2018.

(51) Int. Cl.
| | |
|---|---|
| *A61Q 5/10* | (2006.01) |
| *A61K 8/49* | (2006.01) |
| *A61K 8/46* | (2006.01) |
| *A61Q 5/00* | (2006.01) |

(52) U.S. Cl.
CPC ............ *A61K 8/4946* (2013.01); *A61K 8/463* (2013.01); *A61Q 5/004* (2013.01); *A61Q 5/10* (2013.01); *A61K 2800/4324* (2013.01)

(58) Field of Classification Search
CPC .......... A61Q 5/10; A61Q 5/065; A61K 8/494; A61K 8/49; A61K 8/4946; A61K 8/416; A61K 8/463; A61K 8/4913; A61K 2800/5426

USPC ...................................................... 8/405, 431
See application file for complete search history.

(56) References Cited

U.S. PATENT DOCUMENTS

| | | | |
|---|---|---|---|
| 3,666,403 A | 5/1972 | Shimauchi et al. |
| 5,651,960 A | 7/1997 | Chan et al. |
| 5,708,151 A | 1/1998 | Mockli |
| 6,171,347 B1 | 1/2001 | Kunz et al. |
| 7,208,019 B2 | 4/2007 | Lalleman et al. |
| 7,776,806 B2 | 8/2010 | Tokunaga |
| 8,071,080 B2 | 12/2011 | Giroud |
| 2004/0005286 A1 | 1/2004 | Giroud |
| 2005/0144739 A1 | 7/2005 | Lalleman et al. |
| 2006/0070191 A1 | 4/2006 | Lang et al. |
| 2006/0100114 A1 | 5/2006 | Molenda et al. |

(Continued)

FOREIGN PATENT DOCUMENTS

| | | |
|---|---|---|
| CN | 106420610 A | 2/2017 |
| DE | 10 2005 026355 A1 | 12/2006 |

(Continued)

OTHER PUBLICATIONS

STIC Search Report dated Aug. 26, 2020.*

(Continued)

*Primary Examiner* — Eisa B Elhilo

(74) *Attorney, Agent, or Firm* — The Marbury Law Group, PLLC

(57) ABSTRACT

Provided are methods of treating hair, the method comprising: contacting the hair with a mixture comprising: i. an ionic liquid comprising an imidazolium-based compound or ammonium-based compound, and ii. an anionic surfactant. In certain methods, the mixture further comprises a cationic direct dye.

19 Claims, 12 Drawing Sheets

(56) References Cited

U.S. PATENT DOCUMENTS

| | | | |
|---|---|---|---|
| 2007/0124872 A1* | 6/2007 | Eliu | A61K 8/4926 8/406 |
| 2011/0256081 A1 | 10/2011 | Hawkes et al. | |
| 2015/0328116 A1 | 11/2015 | Patel et al. | |
| 2015/0335548 A1 | 11/2015 | Patel et al. | |
| 2016/0177222 A1 | 6/2016 | Bianchetti et al. | |
| 2016/0367462 A1* | 12/2016 | Samain | A61K 8/4946 |
| 2017/0252284 A1 | 9/2017 | Kroger Lyons et al. | |

FOREIGN PATENT DOCUMENTS

| | | |
|---|---|---|
| DE | 10 2005 032798 A1 | 1/2007 |
| DE | 10 2005 056155 A1 | 5/2007 |
| EP | 0714954 A2 | 6/1996 |
| FR | 2935266 A1 | 3/2010 |
| FR | 2971153 A1 | 8/2012 |
| FR | 2971155 A1 | 8/2012 |
| FR | 2983073 A1 | 5/2013 |
| KR | 2003-0084158 A | 11/2003 |
| KR | 10-2011-0057647 A | 6/2011 |
| WO | 95/01772 A1 | 1/1995 |
| WO | 95/15144 A1 | 6/1995 |
| WO | 1998/023247 A1 | 6/1998 |
| WO | 2007/059822 A1 | 5/2007 |
| WO | 2013/024099 A1 | 2/2013 |
| WO | 2013/079528 A1 | 6/2013 |
| WO | 2018/065827 A1 | 4/2018 |

OTHER PUBLICATIONS

Non-Final Office Action for copending U.S. Appl. No. 16/399,353, dated Apr. 30, 2020.
Copending U.S. Appl. No. 16/888,835, filed May 31, 2020.
Copending U.S. Appl. No. 16/888,821, filed May 31, 2020.
Porter, M.R., "Handbook of Surfactants," published by Blackie & Son (Glasgow and London), 1991, pp. 116-178.
Co-pending U.S. Appl. No. 16/715,034, filed Dec. 16, 2019.
Co-pending U.S. Appl. No. 16/716,266, filed Dec. 16, 2019.
International Search Report and Written Opinion for counterpart Application No. PCT/US2019/067373, dated Mar. 23, 2020.
Yuan, Jiugang et al., "Enhancing Dye Adsorption of Wool Fibers with 1-butyl-3-methylimidazolium Chloride Ionic Liquid Processing," Textile Research Journal, vol. 80, No. 18, Jun. 30, 2010, pp. 1898-1904.
International Search Report and Written Opinion for counterpart Application No. PCT/US2019/067375, dated Mar. 23, 2020.
Chen, Jingyu et al., "What Happens During Natural Protein Fibre Dissolution in Ionic Liquids," Materials, vol. 7, No. 9, Aug. 28, 2014, pp. 6158-6168.
Nizar, Meksi et al., "A review of progress in the ecological application of ionic liquids in textile processes," Journal of Cleaner Production, vol. 161, May 16, 2017, pp. 105-126.
Parnian, Jafari-Chashmi et al., "The Strong Synergistic Interaction Between Surface Active Ionic Liquid and Anionic Surfactant in the Mixed Micelle Using the Spectrophotometric Method," Journal of Molecular Liquids, vol. 269, Aug. 23, 2018, pp. 816-823.
International Search Report and Written Opinion for counterpart Application No. PCT/US2019/067371, dated Apr. 7, 2020.
International Search Report and Written Opinion for counterpart Application No. PCT/US2020/030115, dated Jul. 30, 2020.
Non-Final Office Action for copending U.S. Appl. No. 16/888,821, dated Nov. 4, 2020.
Non-Final Office Action for copending U.S. Appl. No. 16/888,835, dated Nov. 6, 2020.
Final Office Action for copending U.S. Appl. No. 16/399,353, dated Oct. 16, 2020.
Copending U.S. Appl. No. 16/399,353, filed Dec. 16, 2019.
Final Office Action for copending U.S. Appl. No. 16/888,835, dated Mar. 16, 2021.
Final Office Action for copending U.S. Appl. No. 16/888,821, dated Mar. 16, 2021.
Non-Final Office Action for copending U.S. Appl. No. 16/399,353, dated Jun. 24, 2021.
International Preliminary Report of Patentability for counterpart Application No. PCT/US2019/067371, dated Jul. 1, 2021.

* cited by examiner

METHODS AND COMPOSITIONS FOR IMPROVING HAIR COLOR FASTNESS AND REJUVENATING HAIR COLOR

This application claims priority to U.S. Provisional Patent Application No. 62/784,001, filed Dec. 21, 2018.

TECHNICAL FIELD

The present disclosure generally relates to methods and compositions suitable for use to improve hair color fastness to shampoo and/or to rejuvenate hair color during shampoo. In particular, the present disclosure relates to ionic liquids with surfactants to achieve improved hair color fastness and/or hair color rejuvenation.

BACKGROUND

The process of changing the color of hair, can involve depositing an artificial color onto the hair which provides a different shade or color to the hair, and/or lifting the color of the hair, such as lightening the color of dark hair to lighter shades.

Imparting a color change or color effect on hair can be done using permanent and semi-permanent or temporary hair coloring products. Semi-permanent dyeing uses direct dyes, which are nonionic or ionic dyes and colored compounds capable of producing a more or less pronounced change of the natural color of the hair. These dyes may or may not be used in the presence of an oxidizing agent. In contrast with oxidation dye precursors, a direct dye is a relatively voluminous molecule that does not penetrate easily into the core of the fiber. Although such dyes are resistant to shampoo-washing several times, many consumers seek to improve the color fastness and/or to rejuvenate the hair color in between treatments.

Furthermore, many shades are comprised of a combination of dyes which have differing affinities to the hair throughout washes. Thus, over time, the hair color shifts from the originally color-treated hair as some dyes are leached from the hair more quickly than others.

Thus, there is a desire to provide ways to either prevent dyes from being lost through shampoo washes and/or to otherwise rejuvenate certain dyes in colored hair.

SUMMARY

One aspect of the invention pertains to a method of treating color-treated hair. In one or more embodiments, the method comprises:
  a. contacting the color-treated hair with a mixture comprising:
    i. an ionic liquid comprising an imidazolium-based compound or ammonium-based compound, and
    ii. an anionic surfactant,
wherein the hair is color-treated hair has been pre-dyed with a cationic direct dye.

In one or more embodiments, the ionic liquid comprises an imidazolium-based compound having a structure represented by Formula (I) below:

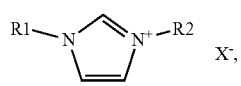

(I)

wherein

R1 and R2 are each independently selected from linear and branched alkyl groups having 1-16 carbon atoms, and X is selected from the group consisting of halides, carboxylates, $C_{1-16}$ fatty acid carboxylates, phosphate, phosphate derivatives, tosylate, tosylate derivatives, sulfate and sulfate derivatives.

In some embodiments, the ionic liquid comprises an imidazolium-based compound selected from the group consisting of butyl-3-methylimidazolium octyl sulfate, butyl-3-methylimidazolium acetate, ethyl-3-methylimidazolium ethylsulfate, 1-ethyl-3-ethyl imidazolium acetate, 1-ethyl-3-methylimidazolium tosylate, and combinations thereof. In one or more embodiments, the ionic liquid comprises an ammonium-based compound having a structure represented by Formula (II) below:

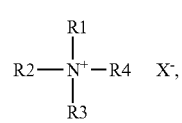

(II)

wherein R1, R2, R3 and R4 are each independently selected from saturated or unsaturated, linear, branched or cyclic groups with the carbon chain length of $C_{1-20}$, which are optionally substituted by one or more hydroxyl, amino $C_{1-4}$ radicals, alkylamino, carboxy, carboxylate, carbamide, $C_{1-4}$ alkoxy, —$SO_3H$, sulfonate or aryl; and X is selected from the group consisting of halides, carboxylates, $C_{1-16}$ fatty acid carboxylates, phosphate, phosphate derivatives, tosylate, tosylate derivatives, sulfate and sulfate derivatives.

In some embodiments, the ionic liquid comprises an ammonium-based compound comprises tributylmethyl ammonium. In one or more embodiments, the cationic dye is hydrophilic. In some embodiments, the hydrophilic dye is selected from the group consisting of Basic Orange 31, Basic Red 51, Basic Yellow 87, Basic Red 76, and combinations thereof. In one or more embodiments, the cationic dye has a negative log $P_{o/w}$ value.

In some embodiments, the cationic dye with negative log $P_{o/w}$ value is selected from the group consisting of Basic Orange 31, Basic Red 51, Basic Yellow 87, and combinations thereof. In one or more embodiments, the surfactant comprises the group consisting of sodium laureth sulfate, alkyl sulfates including sodium lauryl sulfate, sodium dodecyl sulfate and ammonium lauryl sulfate, sulfosuccinates including disodium laureth sulfosuccinate, diethylhexyl sodium sulfosuccinates and dioctyl sodium sulfosuccinate, and combinations thereof. In some embodiments, the surfactant comprises sodium laureth sulfate. In one or more embodiments, the mixture is part of a shampoo composition. In some embodiments, the mixture further comprises the cationic dye that has been used to pre-dye the color-treated hair. In one or more embodiments, the mixture further comprises a second cationic dye.

Another aspect of the invention pertains to a method of treating the hair. The method comprises:
a. contacting the hair with a mixture comprising:
i. an ionic liquid comprising an imidazolium-based compound or ammonium-based compound,
ii. an anionic surfactant, and
iii. a first cationic direct dye.

In some embodiments, the hair has not been pre-dyed. In one or more embodiments, the hair is color-treated hair that has been pre-dyed with a second cationic direct dye, and the first and second cationic direct dyes are the same or different. In some embodiments, the ionic liquid comprises an imidazolium-based compound having a structure represented by Formula (I) below:

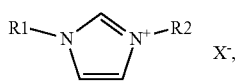

wherein
R1 and R2 are each independently selected from linear and branched alkyl groups having 1-16 carbon atoms, and
X is selected from the group consisting of halides, carboxylates, $C_{1-16}$ fatty acid carboxylates, phosphate, phosphate derivatives, tosylate, tosylate derivatives, sulfate and sulfate derivatives.

In one or more embodiments, the ionic liquid comprises an imidazolium-based compound selected from the group consisting of butyl-3-methylimidazolium octyl sulfate, butyl-3-methylimidazolium acetate, ethyl-3-methylimidazolium ethylsulfate, 1-ethyl-3-ethyl imidazolium acetate, 1-ethyl-3-methylimidazolium tosylate, and combinations thereof. In some embodiments, the ionic liquid comprises an ammonium-based compound having a structure represented by Formula (II) below:

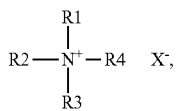

wherein R1, R2, R3 and R4 are each independently selected from saturated or unsaturated, linear, branched or cyclic groups with the carbon chain length of $C_{1-20}$, which are optionally substituted by one or more hydroxyl, amino $C_{1-4}$ radicals, alkylamino, carboxy, carboxylate, carbamide, $C_{1-4}$ alkoxy, —$SO_3H$, sulfonate or aryl; and
X is selected from the group consisting of halides, carboxylates, $C_{1-16}$ fatty acid carboxylates, phosphate, phosphate derivatives, tosylate, tosylate derivatives, sulfate and sulfate derivatives.

In one or more embodiments, the ionic liquid comprises an ammonium-based compound comprises tributylmethyl ammonium. In some embodiments, the cationic dye is hydrophilic. In one or more embodiments, the hydrophilic dye is selected from the group consisting of Basic Orange 31, Basic Red 51, Basic Yellow 87, Basic Red 76, and combinations thereof. In some embodiments, the cationic dye has a negative log Po/w value. In one or more embodiments, the cationic dye with negative log Po/w value is selected from the group consisting of Basic Orange 31, Basic Red 51, Basic Yellow 87, and combinations thereof. In some embodiments, the surfactant comprises the group consisting of sodium laureth sulfate, alkyl sulfates including sodium lauryl sulfate, sodium dodecyl sulfate and ammonium lauryl sulfate, sulfosuccinates including disodium laureth sulfosuccinate, diethylhexyl sodium sulfosuccinates and dioctyl sodium sulfosuccinate, and combinations thereof. In one or more embodiments, the surfactant comprises sodium laureth sulfate. In some embodiments, the mixture is part of a shampoo composition. In one or more embodiments, the first and second cationic direct dye are the same.

DETAILED DESCRIPTION

Figure 1:
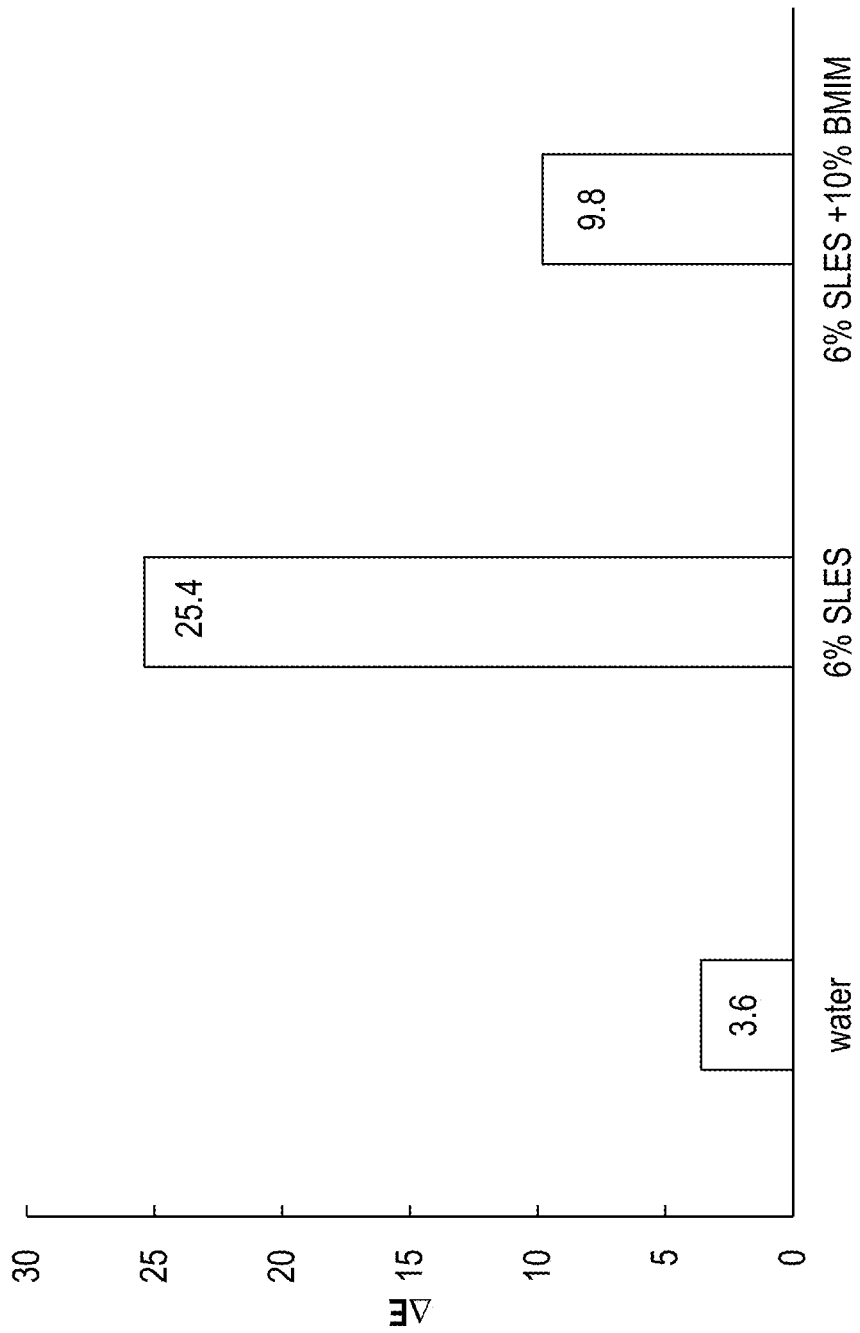
FIG. 1 is a graphical representation of ΔE values of several hair swatches treated with water, surfactant and mixture of ionic liquid and surfactant.
Figure 2:
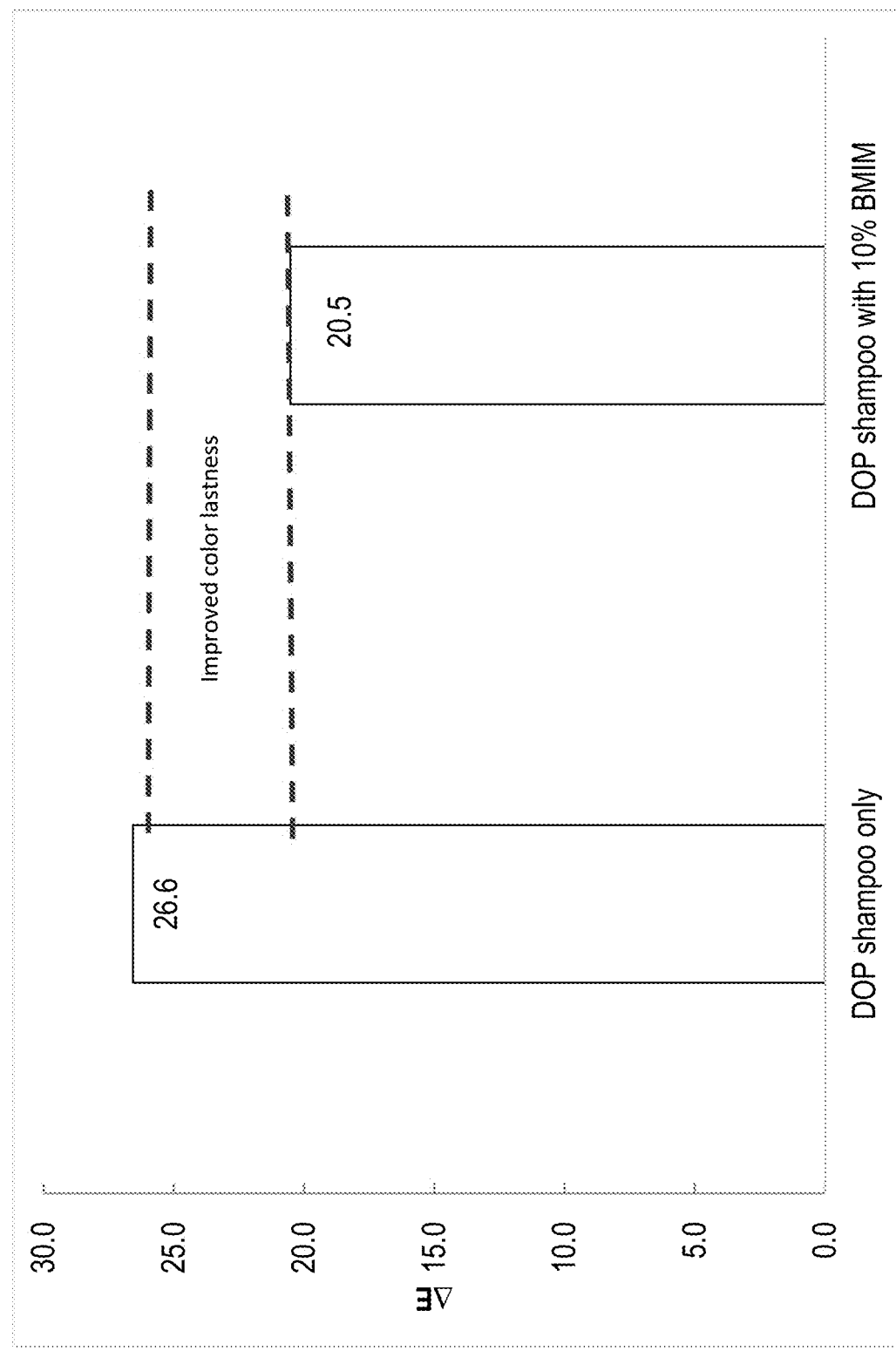
FIG. 2 is a graphical representation of ΔE values of hair swatches treated with a commercially available shampoo and a mixture of the shampoo with the ionic liquid.

As described herein, the disclosure relates to the use of mixtures of certain ionic liquids and anionic surfactants to improve the color fastness of cationic direct dyes from color-treated hair. As used herein, the term "improve color fastness" refers to slowing down the rate that the cationic direct dyes are removed from the color-treated hair when compared to the effect of anionic surfactant alone.

That is, one aspect of the invention pertains to a method of treating color-treated hair, the method comprising:
a. contacting the color-treated hair with a mixture comprising:
  i. an ionic liquid comprising an imidazolium-based compound or ammonium-based compound, and
  ii. an anionic surfactant,
wherein the hair is color-treated hair has been pre-dyed with a cationic direct dye. As used herein, the term "pre-dyed with a cationic direct dye" means the hair has been dyed with a cationic direct dye prior to contact with the mixture comprising ionic liquid and anionic surfactant. As used herein, the term "ionic liquid" refers to an organic salt in the liquid state under 150° C. (preferably 100° C.), or in some embodiments at room temperature. As used herein, the term "contacting" means that the mixture comprising ionic liquid and anionic surfactant comes into contact with the hair so that the mixture is exposed to the direct dye molecules on the hair. In some embodiments, this means the hair can be soaked in the mixture comprising ionic liquid and anionic surfactant, or the hair may be mechanically manipulated with the mixture comprising ionic liquid and anionic surfactant (e.g., using hands to manipulate hair in the presence of the mixture).

It has been surprisingly discovered that such methods allow for the improvement of color fastness. Such effect find utility in shampoos, which often contain such anionic surfactants. Cationic dyes, exhibiting excellent affinity with hair through ionic bonds, are extensively used for semi-permanent coloring. However, this also means that cationic dyes also have strong ionic interactions with anionic surfactants. Thus, the anionic surfactants in shampoos will cause the cationic direct dyes to be removed from color-treated hair at a rate faster than desired by the consumer. The addition of ionic liquids as described herein to anionic surfactant mixtures (e.g., shampoos) slow the rate that the cationic dyes are removed, thereby preserving the shade of the color-treated hair. While not wishing to be bound by any particular theory, it is thought that cations in ionic liquids are capable of forming strong associations with anionic moieties of surfactants and prevents the latter from binding with cationic dyes in the hair. As a result, the removal of cationic dyes from color-treated hair is deterred.

The mixtures may further comprise a cationic direct dye, which is the deposited onto the hair. This can be done to color uncolored hair. Alternatively, this deposition can enhance the color-fastness effect by not only reducing loss of the dye from the hair, but also supplementing it with additional dye.

That is, one aspect of the invention pertains to a method of treating hair, the method comprising:
a. contacting the hair with a mixture comprising:
  i. an ionic liquid comprising an imidazolium-based compound or ammonium-based compound,
  ii. an anionic surfactant, and
  iii. a first cationic direct dye.

In some embodiments, the hair is not color-treated and has not already been dyed. Such embodiments thus pertain to simple deposition of dye onto hair. In alternative embodiments, the hair is color-treated hair has been pre-dyed with a second cationic direct dye, and the first and second cationic direct dyes are the same or different. Such embodiments thus pertain to a rejuvenation of the hair color.

It has thus been surprisingly discovered that the above mixture is useful in rejuvenating the colored hair, particularly when the cationic direct dye present in the mixture is the same as the cationic direct dye present in the color-treated hair. As used herein, the term "rejuvenating" color-treated hair means that color-treated hair is supplemented with additional dye (i.e., the dye present in the mixture compensates for dye lost when exposed to the anionic surfactant).

Alternatively, the composition may be used to deposit the direct dye onto hair to impart a new color. It has thus been surprisingly discovered that the above mixture is useful in general to deposit color onto the hair.

Direct Dyes

Examples of direct dyes include azo direct dyes; (poly)methine dyes such as cyanins, hemicyanins and styryls; carbonyl dyes; azine dyes; nitro(hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:

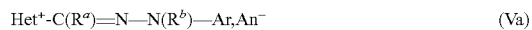  (Va)

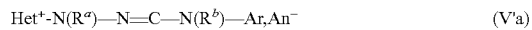  (V'a)

  (VIa)

  (VI'a) and

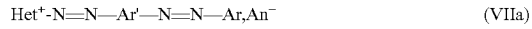  (VIIa)

in which formulas (Va), (V'a), (Via), (VI'a) and (VIIa):

$Het^+$ represents a cationic heteroaryl radical, preferably bearing an endocyclic cationic charge, such as imidazolium, indolium or pyridinium, optionally substituted preferentially with one or more $(C_1-C_8)$ alkyl groups such as methyl;

$Ar^+$ representing an aryl radical, such as phenyl or naphthyl, bearing an exocyclic cationic charge, preferentially ammonium, particularly tri$(C_1-C_8)$alkylammonium such as trimethylammonium;

Ar represents an aryl group, especially phenyl, which is optionally substituted, preferentially with one or more electron-donating groups such as i) optionally substituted $(C_1-C_8)$alkyl, ii) optionally substituted $(C_1-C_5)$ alkoxy, iii) (di)$(C_1-C_8)$(alkyl)amino optionally substituted on the alkyl group(s) with a hydroxyl group, iv) aryl$(C_1-C_8)$alkylamino, v) optionally substituted N—$(C_1-C_8)$alkyl-N-aryl$(C_1-C_8)$alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups $(C_1-C_8)$alkyl, hydroxyl or $(C_1-C_8)$alkoxy Ar" is an optionally substituted (hetero)aryl group such as phenyl or pyrazolyl, which are optionally substituted, preferentially with one or more groups $(C_1-C_8)$alkyl, hydroxyl, (di)$(C_1-C_8)$(alkyl)amino, $(C_1-C_8)$alkoxy or phenyl;

$R^a$ and $R^b$, which may be identical or different, represent a hydrogen atom or a group $(C_1-C_8)$alkyl, which is optionally substituted, preferentially with a hydroxyl group;

or alternatively the substituent $R^a$ with a substituent of $He^r$ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group $(C_1-C_4)$alkyl, which is optionally substituted with a hydroxyl group;

An⁻ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

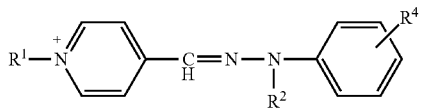
(Va-1)

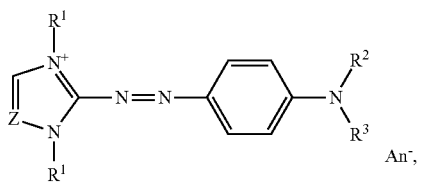
(VIa-1)

formulae (V-1) and (VI-1) with:

$R^1$ representing a ($C_1$-$C_4$) alkyl group such as methyl;

$R^2$ and $R^3$, which are identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$)(alkyl)amino optionally substituted on the alkyl group(s) with a hydroxyl group; particularly, $R^4$ is a hydrogen atom, Z represents a CH group or a nitrogen atom, preferentially CH;

An⁻ represents an anionic counter-ion such as mesylate or halide.

Particularly, the dye of formulae (Va-1) and (Via-1) is chosen from Basic Red 51, Basic Yellow 87 and Basic Orange 31 or derivatives thereof:

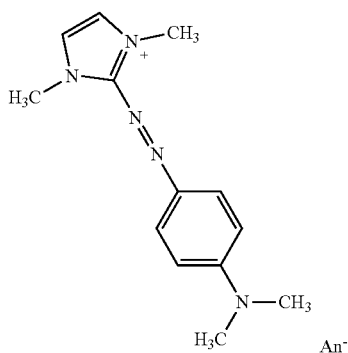
Basic Red 51

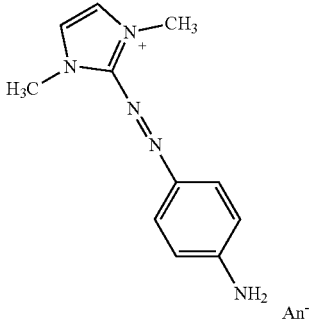
Basic Orange 31

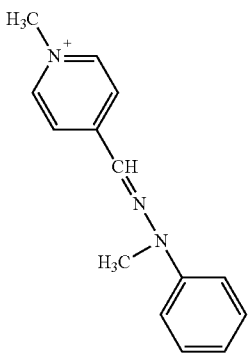
Basic Yellow 87

Non-limiting examples of cationic dyes include Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Non-limiting examples anionic dyes include Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

Non-limiting examples of nitro dyes include HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue 15, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Direct dyes may also be characterized by the partition coefficient (Log $P_{o/w}$) values, which may be calculated as follows:

Log $P_{o/w}$=Log[(dye concentration in octanol)/(dye concentration in water)]

In one or more embodiments, the ionic liquids may be used to direct dyes Log $P_{o/w}$ value which is negative. The Log $P_{o/w}$ values for some dyes follows in the below table.

| DYE NAMES | Log $P_{o/w}$ |
|---|---|
| HC BLUE NO. 2 | −0.32 |
| ACID YELLOW 23 | −10.17 |
| BASIC ORANGE 31 | −2.31 |
| BASIC RED 51 | −1.97 |
| BASIC YELLOW 87 | −1.69 |
| ACID YELLOW 3 | −1.05 |
| HC RED NO. 3 | −0.42 |
| ACID BLUE 9 | −0.32 |
| BASIC BROWN 17 | −0.15 |
| BASIC YELLOW 57 | 0.06 |
| HC RED NO. 7 | 0.13 |
| HC ORANGE NO. 2 | 0.13 |
| 3-NITRO-P-HYDROXYETHYLAMINOPHENOL | 0.21 |
| ACID RED 33 | 0.5 |
| HC VIOLET NO 2 | 0.608 |
| HC VIOLET NO 1 | 0.67 |
| 2-NITRO-5-GLYCERYL METHYLANILINE | 0.89 |
| HYDROXYANTHRAQUINONEAMINO-PROPYL METHYL MORPHOLINIUM METHOSULFATE | 0.89 |
| 3-METHYLAMINO-4-NITROPHENOXYETHANOL | 1.13 |
| 4-AMINO-3-NITROPHENOL | 1.19 |
| HC YELLOW NO. 9 | 1.3 |
| ACID RED 52 | 1.3 |
| ACID ORANGE 7 | 1.4 |
| ACID RED18 | 1.63 |
| BASIC BLUE 99 | 1.88 |
| HC BLUE NO. 14 | 2.09 |
| HC YELLOW NO. 7 | 2.59 |
| DISPERSE VIOLET 1 | 3 |
| ACIDE RED 92 | 3 |
| ACIDE VIOLET 43 | 3.1 |
| EXT VIOLET 2 | 3.1 |
| HC BLUE NO. 15 | 3.47 |
| ACID GREEN 25 | 5.71 |
| ACID BLACK 1 | 1.2 |

Direct dyes which may be advantageously used in the invention may have one or more of the following properties: (1) negative Log Po/w values; (2) contain quaternary moieties in the molecule and have high solubility in water; and/or (3) the dyes predominantly interact with hair fibers through ionic interaction. In some embodiments, the cationic dyes are selected from the group consisting of Basic Orange 31, Basic Red 51, Basic Yellow 87 Basic Red 76, and combinations thereof.

Ionic Liquids
Imidazolium-Based Ionic Liquids

According to one or more embodiments, the ionic liquid comprises an imidazolium-based compound having a structure represented by Formula (I) below:

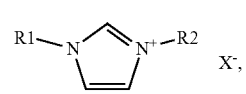

(I)

wherein
R1 and R2 are each independently selected from linear and branched alkyl groups having 1-16 carbon atoms, and
X is selected from the group consisting of halides, carboxylates, $C_{1-16}$ fatty acid carboxylates, phosphate, phosphate derivatives, tosylate, tosylate derivatives, sulfate and sulfate derivatives.

In one or more embodiments, each R group is each independently selected from methyl, ethyl, propyl or butyl. In some embodiments, R2 is methyl, ethyl, propyl, or butyl and R1 is methyl, ethyl, propyl, or butyl, in any combination. Examples include butyl-3-methylimidazolium, butyl-3-methylimidazolium, ethyl-3-methylimidazolium, 1,3-ethyl imidazolium.

In some embodiments, $X^-$ comprises a halide. In further embodiments, the halide comprises $F^-$, $Br^-$, $Cl^-$, or $I^-$. In one or more embodiments, $X^-$ comprises a phosphate, phosphate derivatives, tosylate, tosylate derivatives, sulfate and sulfate derivatives. Such phosphate, tosylate and sulfate derivatives may include alkyl phosphates, alkyl tosylates and alkyl sulfates, respectively. Such phosphate, tosylate and sulfate derivatives may also include halo phosphates, halo tosylates and halo sulfates, respectively. The alkyl groups of such alkyl sulfates could include 1, 2, 3, 4, 5, 6, 7, 8, 9, 10, 11 or 12 carbon atoms. In further embodiments, the alkyl sulfate comprises ethyl sulfate or octyl sulfate. In some embodiments, $X^-$ comprises a carboxylate or fatty acid carboxylate. The fatty acid carboxylate could include 1, 2, 3, 4, 5, 6, 7, 8, 9, 10, 11, 12, 13 or 14 carbon atoms. In further embodiments, the carboxylate comprises acetate.

In some embodiments, the ionic liquid comprises an imidazolium-based compound selected from the group consisting of butyl-3-methylimidazolium octyl sulfate, butyl-3-methylimidazolium acetate, ethyl-3-methylimidazolium ethylsulfate, 1,3-ethyl imidazolium acetate, and combinations thereof.

Ammonium-Based Ionic Liquids

The method of claim 1, wherein the ionic liquid comprises an ammonium-based compound having a structure represented by Formula (II) below:

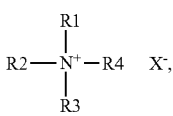

(II)

wherein R1, R2, R3 and R4 are each independently selected from saturated or unsaturated, linear, branched or cyclic groups with the carbon chain length of $C_{1-20}$, which are optionally substituted by one or more hydroxyl, amino $C_{1-4}$ radicals, alkylamino, carboxy, carboxylate, carbamide, $C_{1-4}$ alkoxy, —$SO_3H$, sulfonate or aryl; and X is selected from the group consisting of halides, carboxylates, $C_{1-16}$ fatty acid carboxylates, phosphate, phosphate derivatives, tosylate, tosylate derivatives, sulfate and sulfate derivatives.

In one or more embodiments, R1 is methyl, ethyl, propyl, butyl, pentyl, hexyl, heptyl, octyl, nonyl, decyl, undecyl, dodecyl, trydecyl, tetradecyl, pentadecyl, hexadecyl, heptadecyl, octadecyl, nonadecyl or eicosyl; R2 is methyl, ethyl, propyl, butyl, pentyl, hexyl, heptyl, octyl, nonyl, decyl, undecyl, dodecyl, trydecyl, tetradecyl, pentadecyl, hexadecyl, heptadecyl, octadecyl, nonadecyl or eicosyl; R3 is methyl, ethyl, propyl, butyl, pentyl, hexyl, heptyl, octyl, nonyl, decyl, undecyl, dodecyl, trydecyl, tetradecyl, pentadecyl, hexadecyl, heptadecyl, octadecyl, nonadecyl or eicosyl; and R4 is methyl, ethyl, propyl, butyl, pentyl, hexyl, heptyl, octyl, nonyl, decyl, undecyl, dodecyl, trydecyl, tetradecyl, pentadecyl, hexadecyl, heptadecyl, octadecyl, nonadecyl or eicosyl in any combination.

In some embodiments, $X^-$ comprises a halide. In further embodiments, the halide comprises $F^-$, $Br^-$, $Cl^-$, or $I^-$. In one or more embodiments, $X^-$ comprises a phosphate, phosphate derivatives, tosylate, tosylate derivatives, sulfate and sulfate derivatives. Such phosphate, tosylate and sulfate derivatives may include alkyl phosphates, alkyl tosylates and alkyl sulfates, respectively. Such phosphate, tosylate and sulfate derivatives may also include halo phosphates, halo tosylates and halo sulfates, respectively. The alkyl groups of such alkyl sulfates could include 1, 2, 3, 4, 5, 6, 7, 8, 9, 10, 11 or 12 carbon atoms. In further embodiments, the alkyl sulfate comprises ethyl sulfate or octyl sulfate. In some embodiments, $X^-$ comprises a carboxylate or fatty acid carboxylate. The fatty acid carboxylate could include 1, 2, 3, 4, 5, 6, 7, 8, 9, 10, 11, 12, 13 or 14 carbon atoms. In further embodiments, the carboxylate comprises acetate.

In one or more embodiments, the ionic liquid comprises an ammonium-based compound comprises tributylmethyl ammonium.

Anionic Surfactant

The term "anionic surfactant" means a surfactant comprising, as ionic or ionizable groups, only anionic groups. A species is termed as being "anionic" when it bears at least one permanent negative charge or when it can be ionized as a negatively charged species, under the conditions of use of the composition (for example the medium or the pH) and not comprising any cationic charge. These anionic groups may be chosen from $—CO_2H$, $—CO_2^-$, $—SO_3H$, $—SO_3^-$, $—OSO_3H$, $—OSO_3^-$, $—H_2PO_3$, $—HPO_3^-$, $—PO_3^{2-}$, $—H_2PO_2$, $=HPO_2$, $—HPO_2^-$, $=PO_2^-$, $=POH$, and $=PO^-$ groups.

The anionic surfactants may be sulfate, sulfonate and/or carboxylic (or carboxylate) surfactants, or mixtures thereof.

Sulfate anionic surfactants comprise at least one sulfate function but do not comprise any carboxylate or sulfonate functions. The sulfate anionic surfactants that may be used comprise at least one sulfate function ($—OSO_3H$ or $—OSO_3$).

They may be chosen from the following compounds: alkyl sulfates, alkyl ether sulfates, alkylamido ether sulfates, alkylaryl polyether sulfates, monoglyceride sulfates; and also the salts of these compounds; the alkyl groups of these compounds comprising from 6 to 30 carbon atoms, especially from 12 to 28, better still from 14 to 24 or even from 16 to 22 carbon atoms; the aryl group preferably denoting a phenyl or benzyl group; these compounds possibly being polyoxyalkylenated, especially polyoxyethylenated, and then preferably comprising from 1 to 50 ethylene oxide units and better still from 2 to 10 ethylene oxide units.

Preferentially, the sulfate anionic surfactants are chosen, alone or as a mixture, from:
alkyl sulfates, especially of C6-C24 or even C12-C20,
alkyl ether sulfates, especially of C6-C24 or even C12-C20, preferably comprising from 2 to 20 ethylene oxide units;
in particular in the form of alkali metal or alkaline-earth metal, ammonium or amino alcohol salts.

Sulfonate anionic surfactants comprise at least one sulfonate function ($—SO_3H$ or $—SO_3^-$) and may optionally also comprise one or more sulfate functions, but do not comprise any carboxylate functions. The sulfonate anionic surfactants that may be used comprise at least one sulfonate function ($—SO_3H$ or $—SO_3^-$).

They may be chosen from the following compounds: alkylsulfonates, alkylamidesulfonates, alkylarylsulfonates, α-olefinsulfonates, paraffin sulfonates, alkylsulfosuccinates, alkyl ether sulfosuccinates, alkylamidesulfosuccinates, alkylsulfoacetates, N-acyltaurates, acylisethionates; alkylsulfolaurates; and also the salts of these compounds; the alkyl groups of these compounds comprising from 6 to 30 carbon atoms, especially from 12 to 28, better still from 14 to 24 or even from 16 to 22 carbon atoms; the aryl group preferably denoting a phenyl or benzyl group; these compounds possibly being polyoxyalkylenated, especially polyoxyethylenated, and then preferably comprising from 1 to 50 ethylene oxide units and better still from 2 to 10 ethylene oxide units.

Preferentially, the sulfonate anionic surfactants are chosen, alone or as a mixture, from:
C6-C24 and especially C12-C20 alkylsulfosuccinates, especially laurylsulfosuccinates;
C6-C24 and especially C12-C20 alkyl ether sulfosuccinates;
(C6-C24)acylisethionates and preferably (C12-C18)acylisethionates,
in particular in the form of alkali metal or alkaline-earth metal, ammonium or amino alcohol salts.

Carboxylate anionic surfactants comprise at least one carboxylic or carboxylate function ($—COOH$ or $—COO^-$) and may optionally also comprise one or more sulfate and/or sulfonate functions. The carboxylic anionic surfactants that may be used thus comprise at least one carboxylic or carboxylate function ($—COOH$ or $—COO^-$).

They may be chosen from the following compounds: acylglycinates, acyllactylates, acylsarcosinates, acylglutamates; alkyl-D-galactosideuronic acids, alkyl ether carboxylic acids, alkyl(C6-30 aryl) ether carboxylic acids, alkylamido ether carboxylic acids; and also the salts of these compounds; the alkyl and/or acyl groups of these compounds comprising from 6 to 30 carbon atoms, especially from 12 to 28, better still from 14 to 24 or even from 16 to 22 carbon atoms; the aryl group preferably denoting a phenyl or benzyl group; these compounds possibly being polyoxyalkylenated, especially polyoxyethylenated, and then preferably comprising from 1 to 50 ethylene oxide units and better still from 2 to 10 ethylene oxide units.

Use may also be made of the C6-C24 alkyl monoesters of polyglycoside-polycarboxylic acids, such as C6-C24 alkyl polyglycoside-citrates, C6-C24 alkyl polyglycoside-tartrates and C6-C24 alkyl polyglycoside-sulfosuccinates, and salts thereof.

Among the above carboxylic surfactants, mention may be made most particularly of polyoxyalkylenated alkyl(amido) ether carboxylic acids and salts thereof, in particular those comprising from 2 to 50 alkylene oxide and in particular ethylene oxide groups, such as the compounds sold by the company Kao under the name Akypo.

The polyoxyalkylenated alkyl(amido) ether carboxylic acids that may be used are preferably chosen from those of formula (1):

$$R_1-(OC_2H_4)_n-OCH_2COOA \quad (1)$$

wherein:
R¹ represents a linear or branched C6-C24 alkyl or alkenyl radical, an alkyl(C8-C9)phenyl radical, a radical R2CONH—CH2-CH2- with R2 denoting a linear or branched C9-C21 alkyl or alkenyl radical, preferably, R1 is a C8-C20 and preferably C8-C18 alkyl radical, and aryl preferably denotes phenyl,
n is an integer or decimal number (average value) ranging from 2 to 24 and preferably from 2 to 10,
A denotes H, ammonium, Na, K, Li, Mg or a monoethanolamine or triethanolamine residue.

It is also possible to use mixtures of compounds of formula (1), in particular mixtures of compounds containing different groups R1.

The polyoxyalkylenated alkyl(amido) ether carboxylic acids that are particularly preferred are those of formula (1) in which:
R1 denotes a C12-C14 alkyl, cocoyl, oleyl, nonylphenyl or octylphenyl radical,
A denotes a hydrogen or sodium atom, and
n varies from 2 to 20 and preferably from 2 to 10.

Even more preferentially, use is made of compounds of formula (1) in which R denotes a C12 alkyl radical, A denotes a hydrogen or sodium atom and n ranges from 2 to 10.

Preferentially, the carboxylic anionic surfactants are chosen, alone or as a mixture, from:
acylglutamates, especially of C6-C24 or even C12-C20, such as stearoylglutamates, and in particular disodium stearoylglutamate;
acylsarcosinates, especially of C6-C24 or even C12-C20, such as palmitoylsarcosinates, and in particular sodium palmitoylsarcosinate;
acyllactylates, especially of C12-C28 or even C14-C24, such as behenoyllactylates, and in particular sodium behenoyllactylate;
C6-C24 and especially C12-C20 acylglycinates;
(C6-C24)alkyl ether carboxylates and especially (C12-C20)alkyl ether carboxylates;
polyoxyalkylenated ($C_6$-$C_{24}$)alkyl(amido) ether carboxylic acids, in particular those comprising from 2 to 50 ethylene oxide groups; in particular in the form of alkali metal or alkaline-earth metal, ammonium or amino alcohol salts.

When the anionic surfactant is in salt form, the said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the anionic surfactants are chosen, alone or as a mixture, from:
C6-C24 and especially C12-C20 alkyl sulfates;
C6-C24 and especially C12-C20 alkyl ether sulfates; preferably comprising from 2 to 20 ethylene oxide units;
C6-C24 and especially C12-C20 alkylsulfosuccinates, especially laurylsulfosuccinates;
C6-C24 and especially C12-C20 alkyl ether sulfosuccinates;
(C6-C24)acylisethionates and preferably (C12-C18)acylisethionates;
C6-C24 and especially C12-C20 acylsarcosinates; especially palmitoylsarcosinates;
(C6-C24)alkyl ether carboxylates, preferably (C12-C20) alkyl ether carboxylates;
polyoxyalkylenated (C6-C24)alkyl(amido) ether carboxylic acids and salts thereof, in particular those comprising from 2 to 50 alkylene oxide and in particular ethylene oxide groups;
C6-C24 and especially C12-C20 acylglutamates;
C6-C24 and especially C12-C20 acylglycinates;
in particular in the form of alkali metal or alkaline-earth metal, ammonium or amino alcohol salts.

In particular, ($C_{12}$-$C_{20}$)alkyl sulfates, ($C_{12}$-$C_{20}$)alkyl ether sulfates comprising from 2 to 20 ethylene oxide units, especially in the form of alkali metal, ammonium, amino alcohol and alkaline-earth metal salts, or a mixture of these compounds, may be chosen. In at least one embodiment, sodium lauryl ether sulfate containing 2.2 mol of ethylene oxide is chosen.

In other embodiments, the anionic surfactant is chosen from sodium laureth sulfate, sodium lauryl sulfate, sodium lauroyl methyl isethionate, and mixtures thereof.

Concentrations

In one or more embodiments, the ionic liquid may be present at a concentration ranging from about 0.01, 0.1, 0.2, 0.3, 0.4, 0.5, 1, 2, 3, 4, 5, 6, 7, 8, 9, 10, 11, 12, 13, 14, 15, 16, 17, 19, 20, 25, 30, 35 or 40 to about 1, 2, 3, 4, 5, 6, 7, 8, 9, 10, 11, 12, 13, 14, 15, 16, 17, 19, 20, 25, 30, 35, 40, 45, 50, 55, 60, 65 or 70 wt. % by total weight of the composition. In one or more embodiments, the surfactant may be present at a concentration ranging from about 0.01, 0.1, 0.2, 0.3, 0.4, 0.5, 1, 2, 3, 4, 5, 6, 7, 8, 9, 10, 11, 12, 13, 14, 15, 16, 17, 19, 20, 25, 30, 35 or 40 to about 0.5, 1, 2, 3, 4, 5, 6, 7, 8, 9, 10, 11, 12, 13, 14, 15, 16, 17, 19, 20, 25, 30, 35, 40, 45, 50, 55, 60, 65 or 70 wt. % by total weight of the composition. When present in the mixture of the ionic liquid and anionic surfactant, the cationic dye may be present at a concentration ranging from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 1, 2, 3, 4, 5, 6, 7, 8, 9, or 10 to about 0.1, 0.2, 0.3, 0.4, 0.5, 1, 2, 3, 4, 5, 6, 7, 8, 9, 10, 11, 12, 13, 14, 15, 16, 17, 19, 20, 25, 30, 35 or 40 wt. % by total weight of the composition.

Additional Components

The composition according to the disclosure may also comprise additives chosen from anionic polymers, nonionic polymers, rheology modifiers, thickening and/or viscosity modifying agents, associative or non-associative polymeric thickeners, non-polymeric thickeners, non-polymeric cationic surfactants, nacreous agents, dyes or pigments, fragrances, mineral, plant or synthetic oils, waxes, vitamins, proteins including ceramides, vitamins, UV-screening agents, free-radical scavengers, antidandruff agents, hair-loss counteractants, hair restorers, preserving agents, pH stabilizers and solvents, and mixtures thereof. A person skilled in the art will take care to select the optional additives and the amount thereof such that they do not harm the properties of the compositions of the present disclosure.

If present in the composition, these additives are generally present in an amount ranging up to about 40% by weight of active material relative to the total weight of the composition, such as up to about 30%, up to about 20%, up to about 15%, up to about 10%, up to about 5%, such as from 0% to 20%.

The compositions of certain embodiments may comprise stabilizers, for example sodium chloride, magnesium dichloride or magnesium sulfate.

The rheology modifiers and thickening/viscosity-modifying agents that may be employed in compositions of the present disclosure may include any water-soluble or water-dispersible compound that is compatible with the compositions of the disclosure, such as acrylic polymers, non-acrylic polymers, starch, cellulose-based polymers, non-polymeric and polymeric gelling agents, and mixtures thereof.

EXAMPLES

The ingredient amounts in the composition/formulations described below are expressed in % by weight, based on the total weight of the composition, unless otherwise indicated.

Color Fastness Examples

Several ionic liquids were tested for efficacy for improving the color fastness to shampoos of several direct dyes. The ionic liquids tested are indicated in the table below.

| Ionic Liquids Tested | |
|---|---|
| Name | Structure |
| Butyl-3-methylimidazolium acetate (BMIM OAc) | |
| Ethyl-3-methylimidazolium ethylsulfate (EMIM ethylsulfate) | |

Unless otherwise indicated, the formulations described contained the active ingredients listed with the balance made up of water.

Unless otherwise indicated, hair swatches were all treated using the same protocol. Specifically, 2 g dyed hair swatches are soaked in 80 g treatment solution for 30 minutes at room temperature. The treated hair swatches are then shampooed once and blow-dried for evaluation.

Unless otherwise indicated, color retention efficacy is measured using CIE L*a*b* coordinates. ΔE is used to describe the color difference and is defined by the following equation:

$$\Delta E_{ab}^* = \sqrt{(L_2^* - L_1^*)^2 + (a_2^* - a_1^*)^2 + (b_2^* - b_1^*)^2},$$

where, $L_1^*$, $a_1$, $b_1$ are measured on freshly dyed hair, $L_2^*$, $a_2$, $b_2$ are measured on the dyed hair treated by the ionic liquid and surfactant mixtures. The lower the ΔE values, the more efficient the color retention.

Example 1—Color Fastness of Basic Orange 31 Treated with BMIM OAc and SLES

Orange 31 contains a quaternary moiety, and has the structure below. The Log Po/w value around −2.31. Based on the structure, it is speculated that basic orange 31 predominately interacts with hair through strong ionic interaction.

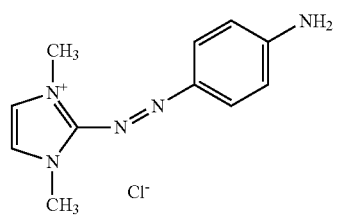 [SMILES: Cn1cc[n+](C)c1N=Nc1ccc(N)cc1 ; [Cl-]]

Hair swatches dyed with Basic Orange 31 were treated with BMIM OAc and sodium laureth sulfate (SLES) using the protocol described above. The resulting ΔE are shown in FIG. 1. As seen from the FIG. 1, with addition of BMIM OAc to 6% SLES, the ΔE value decreases, indicating that color fastness of Basic Orange 31 has improved.

Figure 7:
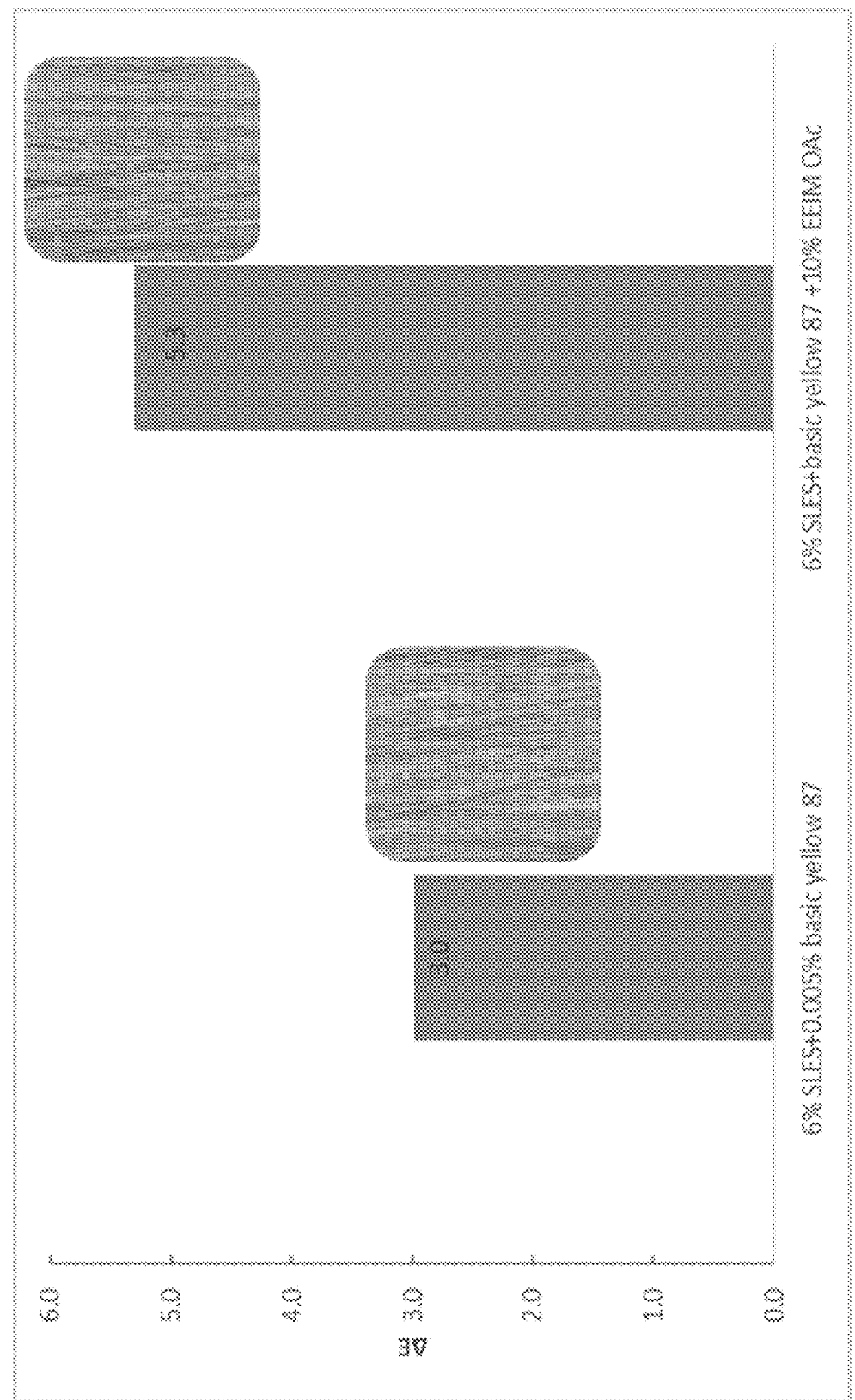
FIG. 7 is a graphical representation of ΔE values of two hair swatches treated with a mixture of surfactant and dye and a mixture of surfactant, dye and ionic liquid.

To further verify the benefit of BMIM OAc improving color fastness of Basic Orange 31, 10% BMIM OAc was added to DOP shampoo, which is a commercially available shampoo containing about 9% SLES. Hair swatches were washed 10× with the shampoo containing BMIM OAc. ΔE values are shown in FIG. 7. As seen in FIG. 7, addition of BMIM OAc to the DOP shampoo prevent Basic Orange 31 from leaching out of hair fibers.

Example 2—Color Fastness of Basic Red 51 Treated With EMIM Ethylsulfate and SLES Hair swatches dyed with Basic Red 51 were treated with varying concentrations of EMIM ethylsulfate and SLES using the protocol described above. Basic Red 51 contains a quaternary moiety and has the structure below and thought to interact with hair through strong ionic interaction. The Log $P_{o/w}$ value around −1.97.

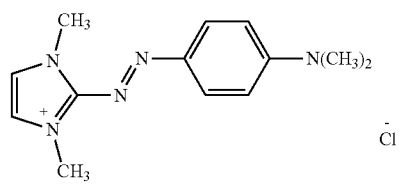

Figure 3:
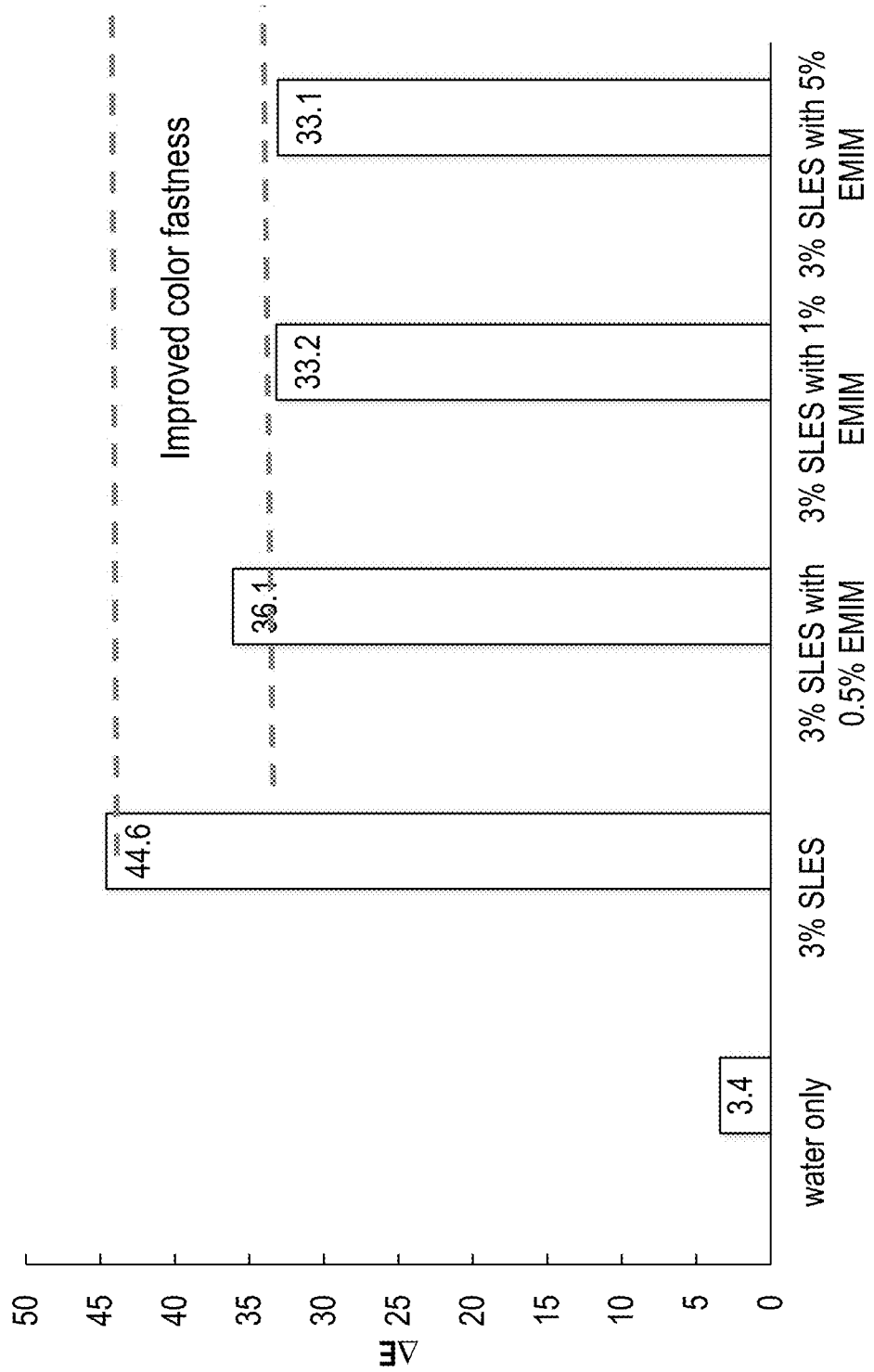
FIG. 3 is a graphical representation of ΔE values of several hair swatches treated according to one or more embodiments of the invention as well as comparative.

The resulting ΔE are in FIG. 3. As seen from FIG. 3, with addition of EMIM ethylsulfate at varying concentrations to 3% SLES, the ΔE values decrease with respect to SLES alone, indicating that color fastness of basic red 51 has improved.

Example 3—Color Fastness of Basic Yellow 87 Treated With BMIM OAc and SLES

Hair swatches dyed with Basic Yellow 87 were treated with BMIM OAc at 10% concentration using the protocol described above. Basic Yellow 87 has the structure below, and a Log $P_{o/w}$ value around −1.67. It is thought that Basic Yellow 87 predominately interacts with hair through strong ionic interaction.

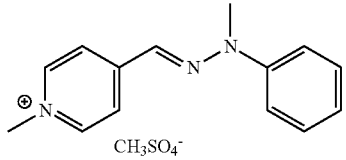

Figure 4:
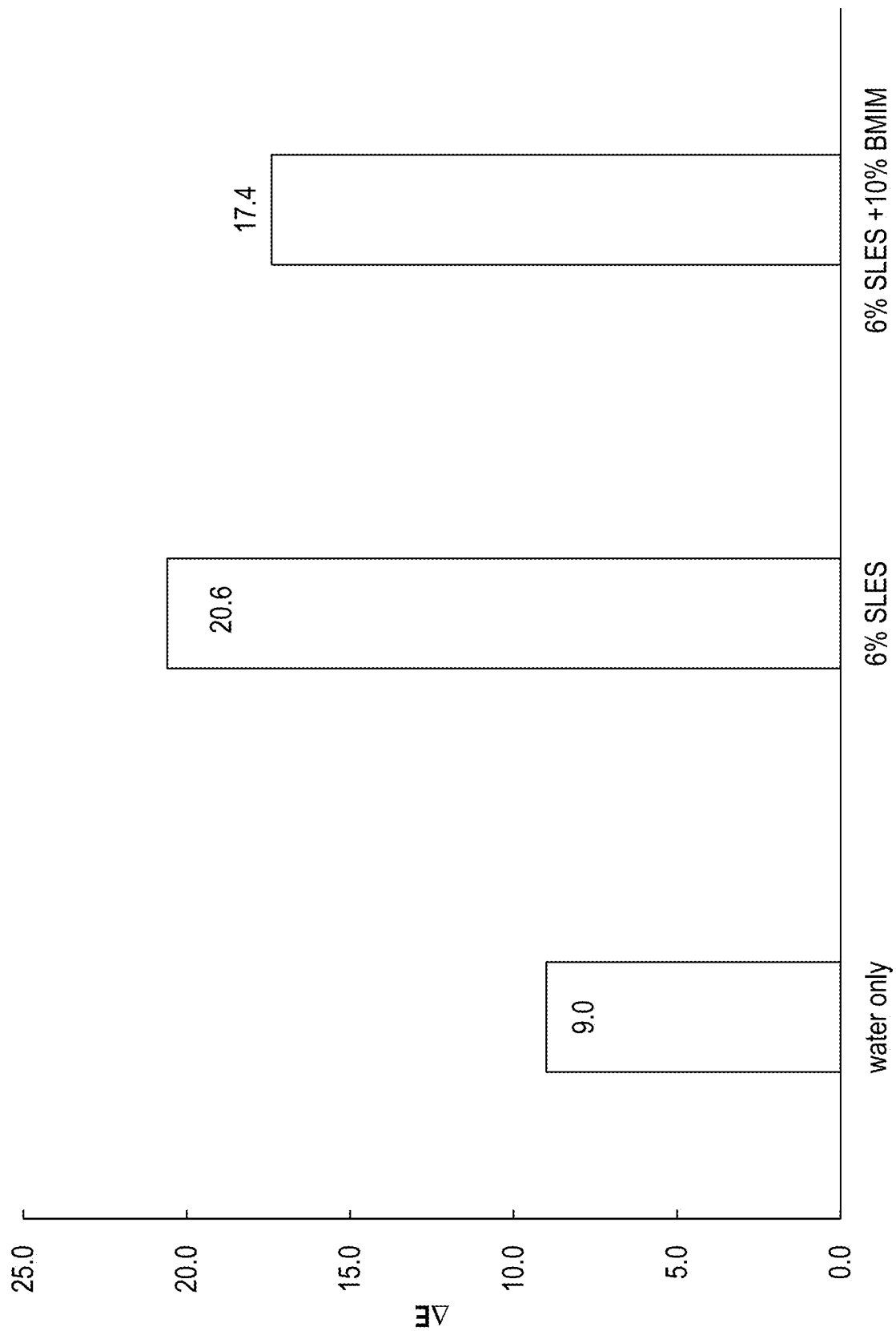
FIG. 4 is a graphical representation of ΔE values of three hair swatches treated with water, surfactant and mixture of ionic liquid and surfactant.

The resulting ΔE are in FIG. 4. As seen from FIG. 4, addition of BMIM OAc to the surfactant improves Basic Yellow 87 color lastingness in hair.

Color Deposition/Rejuvenation Examples

Mixtures of ionic liquids, surfactants and dyes were tested for efficacy for rejuvenating hair color. The ionic liquids tested are indicated in the table below.

Ionic Liquids Tested

| Name | Structure |
| --- | --- |
| Butyl-3-methylimidazolium acetate (BMIM OAc) | 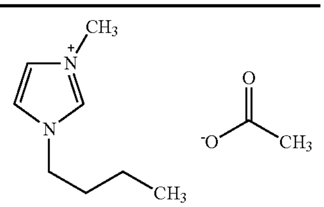 |
| 1,3-Ethyl Imidazolium Acetate (EEIM OAc) | 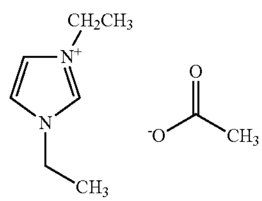 |

Unless otherwise indicated, the formulations described contained the active ingredients listed with the balance made up of water.

Unless otherwise indicated, hair swatches were all treated using the same protocol. Specifically, 2 g platinum bleached hair swatches were soaked in 80 g solutions containing 6% SLES and 0.005% dyes with/without adding 10% ionic liquid for 10 minutes at a room temperature; the treated hair swatches were then shampooed once and blow-dried for evaluation.

Unless otherwise indicated, color deposition efficacy is measured using CIE L*a*b* coordinates. ΔE is used to describe the color difference and is defined by the following equation:

$$\Delta E_{ab}* = \sqrt{(L_2*-L_1*)^2 + (a_2*-a_1*)^2 + (b_2*-b_1*)^2},$$

where, $L_1*$, $a_1$, $b_1$ are measured on undyed hair; $L_2*$, $a_2$, $b_2$ are measured on hair treated by the surfactant containing ionic liquid and dyes. Higher ΔE values indicate more efficient dye deposition.

Example 4—Color Deposition/Rejuvenation of Basic Orange 31 Using 1,3-Ethyl Imidazolium Acetate (EEIM OAc) and SLES Hair swatches dyed with Basic Orange 31 (Log $P_{o/w}$ value around −2.31) were treated with EEIM OAc and sodium laureth sulfate (SLES) and compared to a sample with SLES and Basic Orange 31 only using the protocol described above. The resulting ΔE values are shown in FIG. 5.

Figure 5:
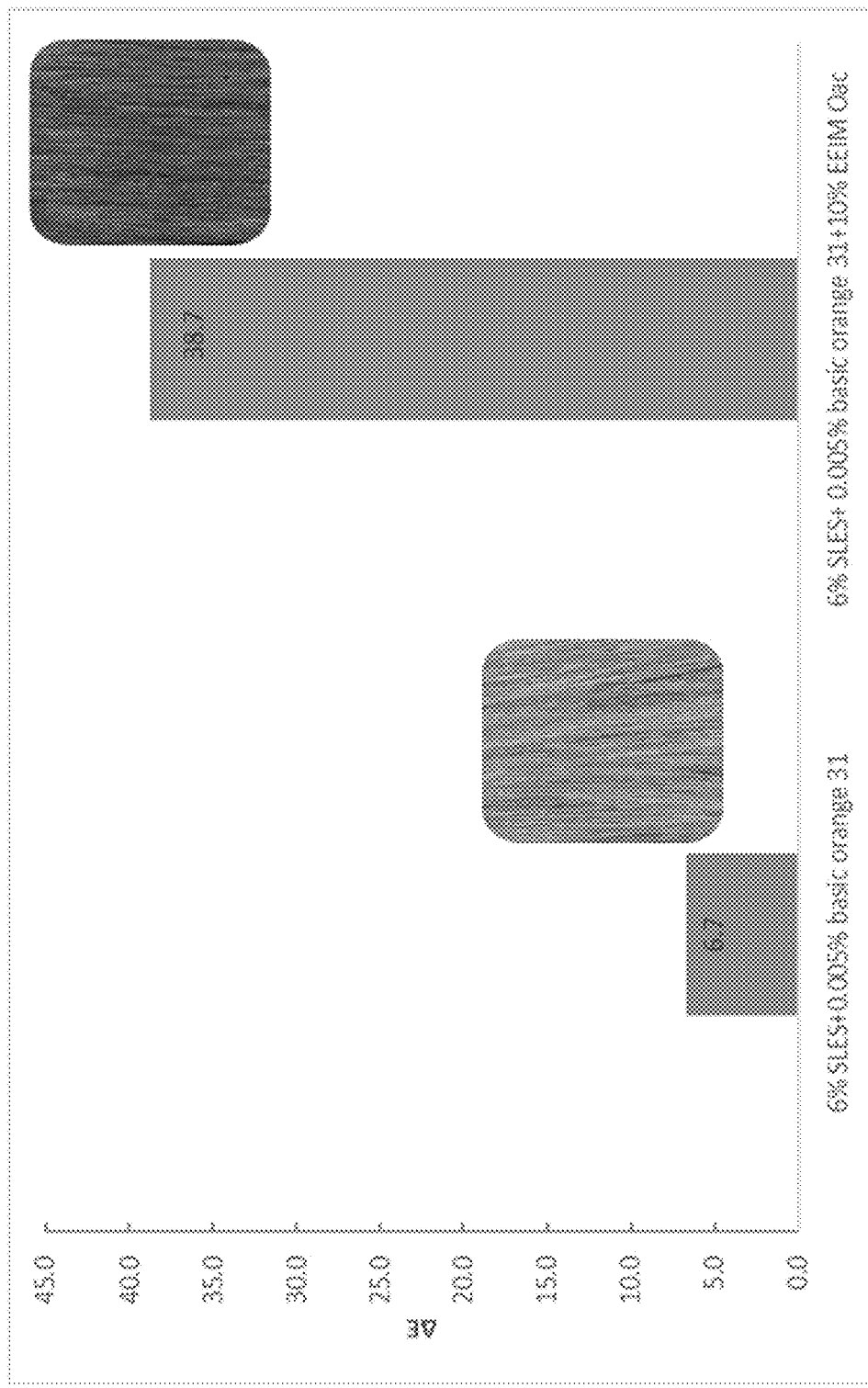
FIG. 5 is a graphical representation of ΔE values of two hair swatches treated with a mixture of surfactant and dye and a mixture of surfactant, dye and ionic liquid.

As seen from FIG. 5, with addition of EEIM OAc to 6% SLES, the ΔE value significantly increases, indicating that EEIM OAc facilitates Basic Orange 31 deposition onto the hair.

Example 5—Color Deposition/Rejuvenation of Basic Red 51 Using 1,3-Ethyl Imidazolium Acetate (EEIM OAc) and SLES Hair swatches dyed with Basic Red 51 (Log $P_{o/w}$ value around −1.97) were treated with EMIM ethylsulfate and SLES and compared to a sample with SLES and Basic Red 51 only using the protocol described above. The resulting ΔE values are shown in FIG. 6.

Figure 6:
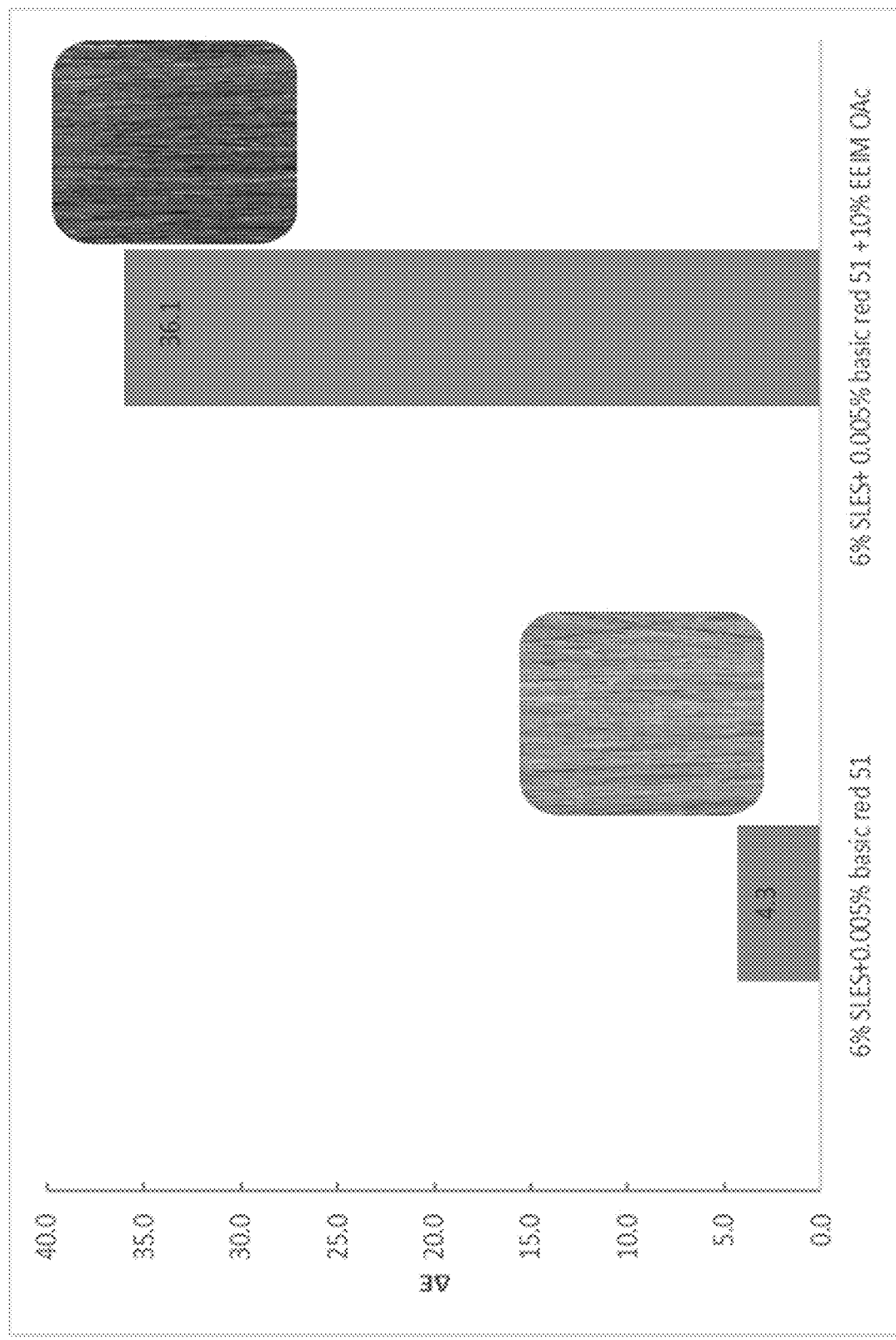
FIG. 6 is a graphical representation of ΔE values of two hair swatches treated with a mixture of surfactant and dye and a mixture of surfactant, dye and ionic liquid.

As seen from FIG. 6, with addition of EEIM OAc, ΔE values significantly increase, indicating that EEIM OAc facilitates Basic Red 51 deposition onto the hair.

Example 6—Color Deposition/Rejuvenation of Basic Yellow 87 Using 1,3-Ethyl Imidazolium Acetate (EEIM OAc) and SLES Hair swatches dyed with Basic Yellow 87 (Log Po/w value around −1.67) were treated with EMIM ethylsulfate and SLES and compared to a sample with SLES and Basic Yellow 87 only using the protocol described above. The resulting ΔE values are shown in FIG. 7.

As seen in FIG. 7, with addition of EEIM OAc, ΔE increases, indicating that EEIM OAc facilitates Basic Yellow 87 deposition onto the hair.

Example 7—Color Deposition/Rejuvenation of Basic Orange 31 Using 1-Butyl-3-Methyl Imidazolium Acetate (BMIM OAc) and SLES Hair swatches dyed with Basic Orange 31 (Log Po/w value around −2.31) were treated with BMIM OAc and sodium laureth sulfate (SLES) and compared to a sample with SLES and Basic Orange 31 only using the protocol described above. The resulting ΔE values are shown in FIG. 8.

Figure 8:
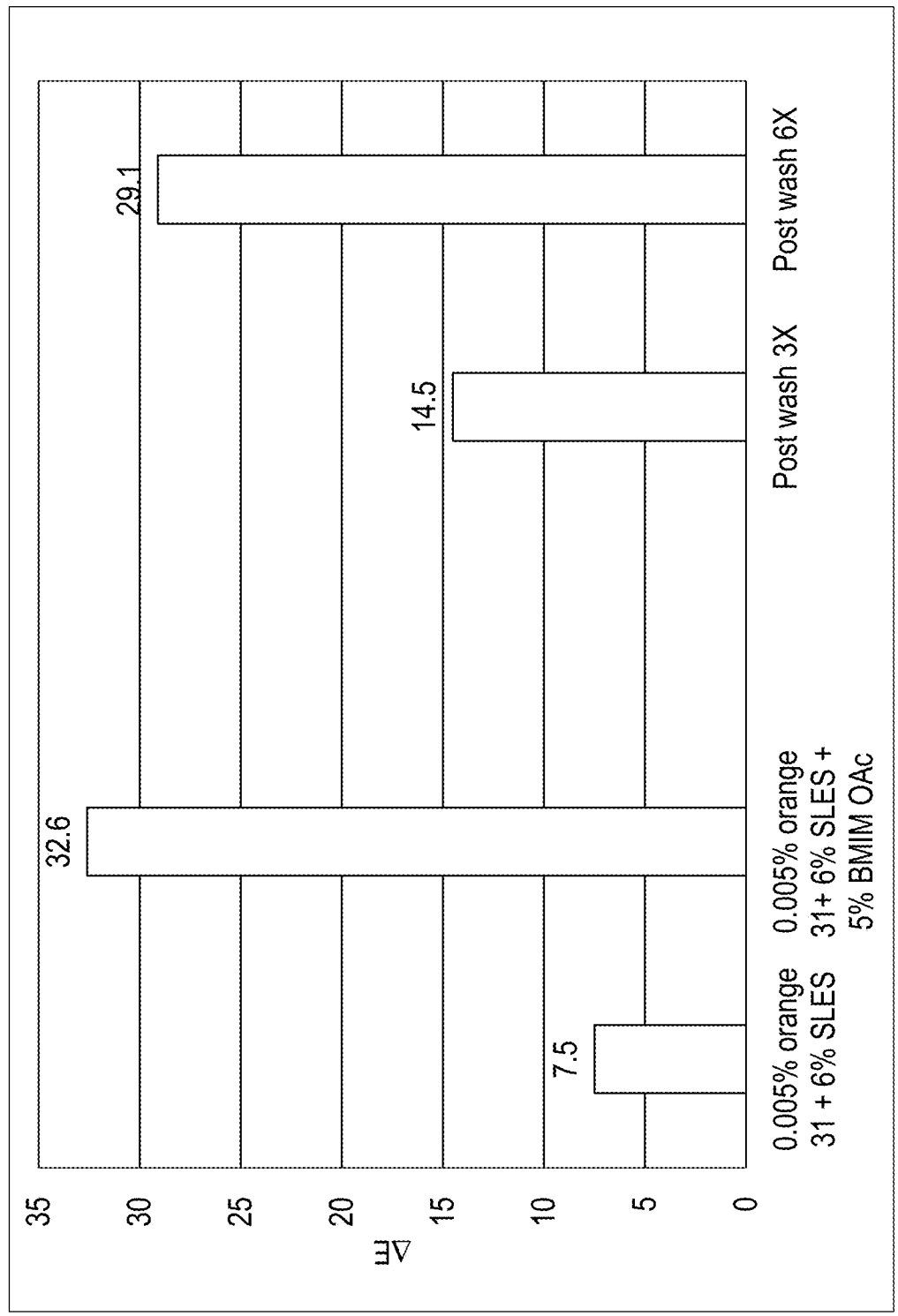
FIG. 8 is a graphical representation of ΔE values of two hair swatches treated with a mixture of surfactant and dye and a mixture of surfactant, dye and ionic liquid, as well as the latter swatch after three and six washes with shampoo.

As seen from FIG. 8, the addition of BMIM OAc to 6% SLES facilitates Basic Orange 31 deposition onto the hair and that deposited Basic Orange 31 can last at least three shampoo washes.

Example 8—Color Deposition/Rejuvenation of Basic Orange 31 Using BMIM OAc in Commercial Color Protection Shampoo BMIM OAc and dye were added into a commercially available shampoo which contains about 12.3 wt. % sodium laureth sulfate and then used to wash hair swatches according to the following protocol: apply the product (1 g product/1 g hair) on wet hair, lather for 30 second, wait for 30 seconds and then rinse it off.

Figure 9:
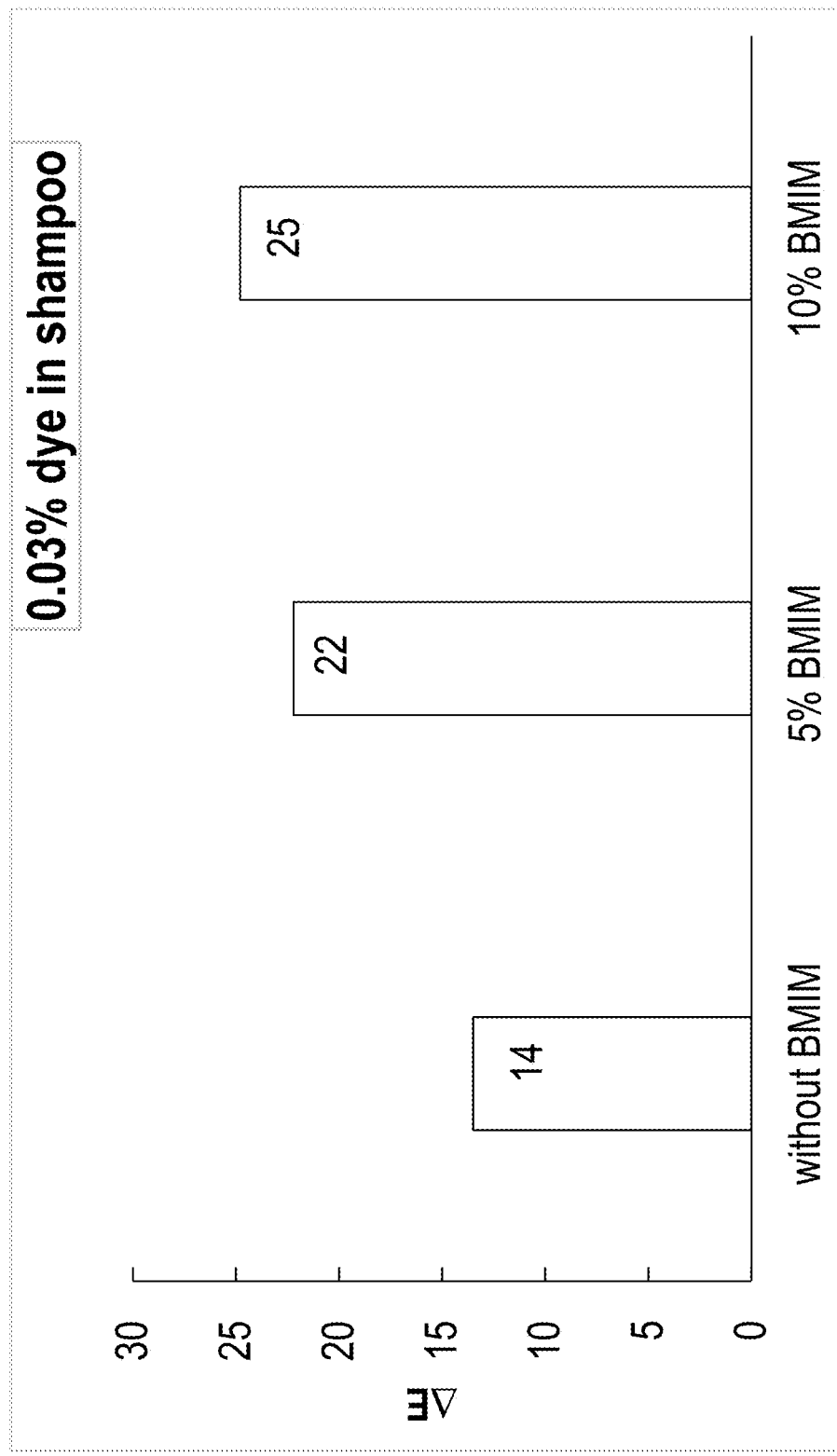
FIG. 9 is a graphical representation of ΔE values of three hair swatches treated with dye in a shampoo, a mixture of dye in a shampoo and an ionic liquid, and a mixture of dye in a shampoo and higher concentration of ionic liquid.

FIG. 9 shows ΔE versus increasing BMIM OAc concentration. As seen, there is a large increase in ΔE with the addition of BMIM OAc as compared to the sample without BMIM OAc.

Figure 10:
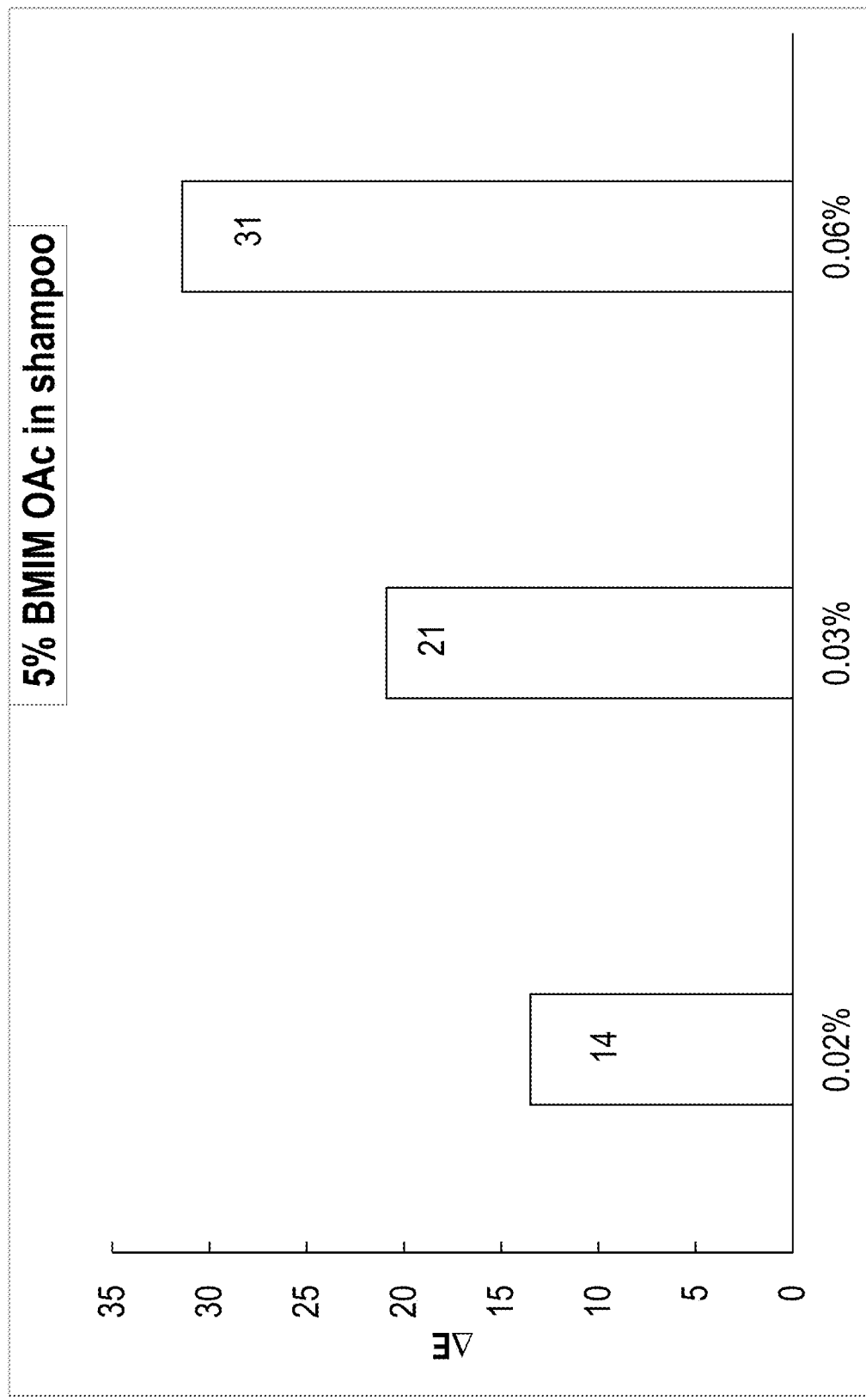
FIG. 10 is a graphical representation of ΔE values of three hair swatches treated with an ionic liquid in a shampoo with varying concentrations of ionic liquid.

FIG. 10 shows ΔE versus increasing dye concentration. As seen, there is a large increase in ΔE with the addition of dye as compared to the sample without BMIM OAc.

Figure 11:
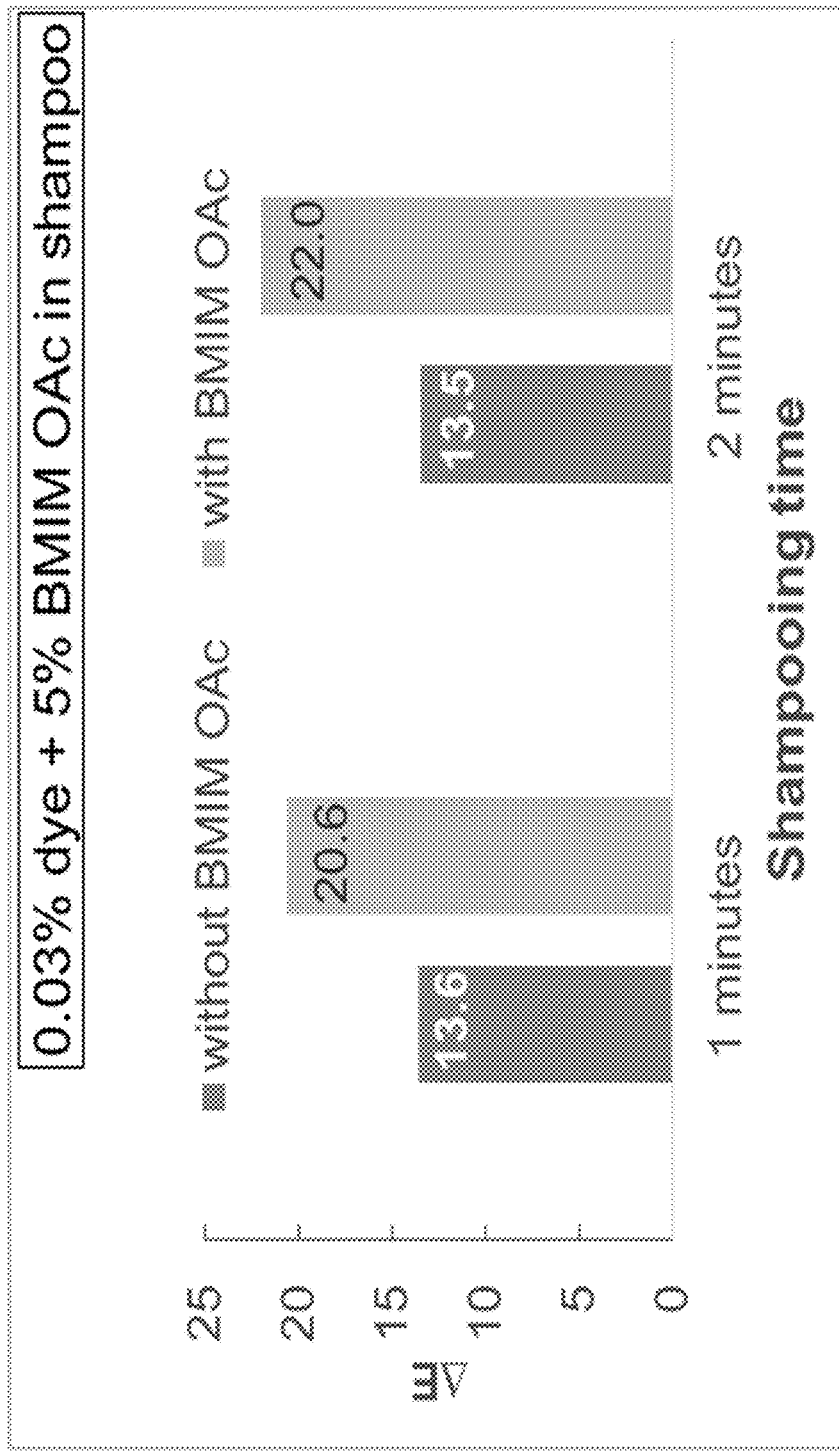
FIG. 11 is a graphical representation of ΔE values of hair swatches treated with a mixture of dye in a shampoo with and without ionic liquid and evaluated after 1 and 2 minutes of washing.

FIG. 11 shows ΔE versus increasing shampoo time. As seen, the ΔE values remain fairly constant between one and two minutes when swatches are washed with the shampoo without BMIM OAc. However, the presence of BMIM OAc greatly increases the ΔE values over the shampoo without BMIM OAc, as well as increasing the ΔE with just one more minute of washing. Thus, deposition appears to occur relatively rapidly.

Figure 12:
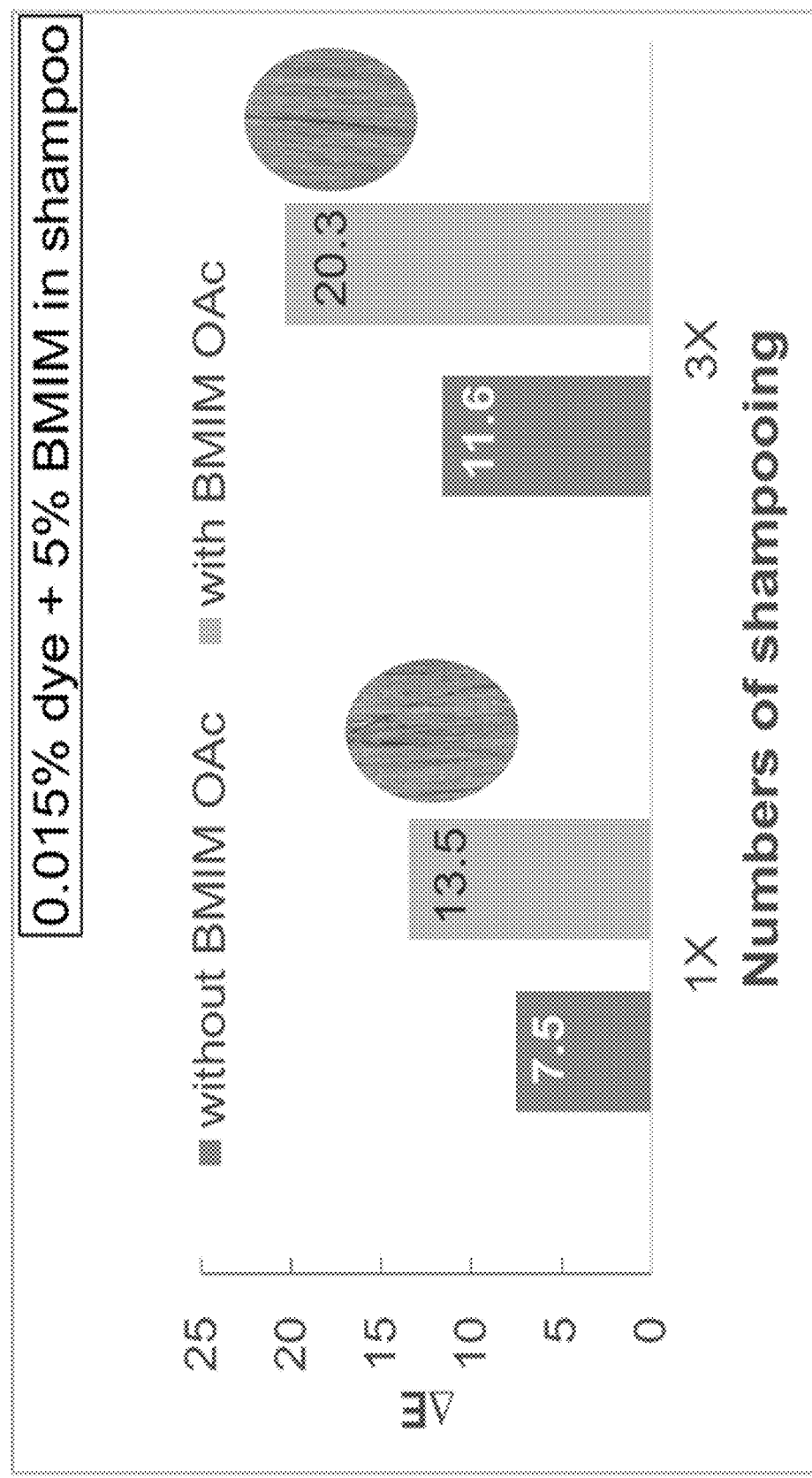
FIG. 12 is a graphical representation of ΔE values of hair swatches treated with a mixture of dye in a shampoo with and without ionic liquid and evaluated after 1 and 3 washes.

FIG. 12 shows ΔE versus increasing shampoo sessions for swatches washed with and without BMIM OAc. As seen, the ΔE values increase for both samples with repeated washing. However, the samples with BMIM OAc show significantly higher ΔE values compared to the samples without BMIM OAc. This indicates a significant buildup of dye onto the hair with repeated use.

Other than in the operating examples, or where otherwise indicated, all numbers expressing quantities of ingredients and/or reaction conditions are to be understood as being modified in all instances by the term "about" which can encompass ±10%, ±8%, ±6%, ±5%, ±4%, ±3%, ±2%, ±1%, or ±0.5%.

All numbers expressing pH values are to be understood as being modified in all instances by the term "about" which encompasses up to +3%.

"At least one" as used herein means one or more and thus includes individual components as well as mixtures/combinations.

The term "altering the color" or "color-altering" as used herein may refer to lifting or lightening the color of hair. It can also refer to dyeing or coloring hair or depositing color onto the hair. In certain instances, it refers to lifting or lightening the color of hair and depositing color onto the hair in one treatment.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The term "neutralized" as used herein is intended to mean that the 3-butoxypropylamine is protonated with a H+ (proton) coming from the diacid(s).

The term "substantially free of (a component)" as defined herein means that the system or composition contains no appreciable amount of the component, for example, no more than about 1% by weight, no more than about 0.5% by weight, or no more than about 0.3% by weight, such as no more than about 0.1% by weight, based on the weight of the composition.

The term "free" or "completely free of (a component)" as defined herein means that the composition does not contain the component in any measurable degree by standard means.

What is claimed is:

1. A method of treating color-treated hair, the method comprising:
   a. contacting the color-treated hair with a mixture comprising:
      i. at least one ionic liquid comprising an imidazolium-based compound or ammonium-based compound, and
      ii. at least one anionic surfactant,
   wherein the hair is color-treated hair that has been pre-dyed with at least one cationic direct dye.

2. The method of claim 1, wherein the at least one ionic liquid comprises an imidazolium-based compound having a structure represented by Formula (I) below:

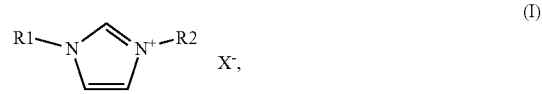

wherein
R1 and R2 are each independently selected from linear and branched alkyl groups having 1-16 carbon atoms, and
X is selected from halides, carboxylates, $C_{1-16}$ fatty acid carboxylates, phosphate, phosphate derivatives, tosylate, tosylate derivatives, sulfate, or sulfate derivatives.

3. The method of claim 2, wherein the ionic liquid comprises an imidazolium-based compound selected from 1-butyl-3-methylimidazolium octyl sulfate, 1-butyl-3-methylimidazolium acetate, 1-ethyl-3-methylimidazolium ethylsulfate, 1-ethyl-3-ethyl imidazolium acetate, 1-ethyl-3-methylimidazolium tosylate, or combinations thereof.

4. The method of claim 1, wherein the ionic liquid comprises an ammonium-based compound having a structure represented by Formula (II) below:

wherein R1, R2, R3 and R4 are each independently selected from saturated or unsaturated, linear, branched or cyclic groups with a carbon chain length of $C_{1-20}$, which are optionally substituted by one or more hydroxyl, amino $C_{1-4}$ radicals, alkylamino, carboxy, carboxylate, carbamide, $C_{1-4}$ alkoxy, —$SO_3H$, sulfonate or aryl; and
X is selected from halides, carboxylates, $C_{1-16}$ fatty acid carboxylates, phosphate, phosphate derivatives, tosylate, tosylate derivatives, sulfate, or sulfate derivatives.

5. The method of claim 4, wherein the ionic liquid comprises an ammonium-based compound comprising tributylmethyl ammonium.

6. The method of claim 1, wherein the cationic dye is hydrophilic, and wherein the hydrophilic dye is selected from Basic Orange 31, Basic Red 51, Basic Yellow 87, Basic Red 76, or combinations thereof.

7. The method of claim 1, wherein the cationic dye has a negative log $P_{o/w}$ value, and wherein the cationic dye with negative log $P_{o/w}$ value is selected from Basic Orange 31, Basic Red 51, Basic Yellow 87, or combinations thereof.

8. The method of claim 1, wherein the anionic surfactant is selected from sodium laureth sulfate, alkyl sulfates including sodium lauryl sulfate, sodium dodecyl sulfate and ammonium lauryl sulfate, sulfosuccinates including disodium laureth sulfosuccinate, diethylhexyl sodium sulfosuccinates, dioctyl sodium sulfosuccinate, or combinations thereof.

9. The method of claim 1, wherein the mixture further comprises the cationic dye that has been used to pre-dye the color-treated hair.

10. The method of claim 1, wherein the mixture further comprises a second cationic dye.

11. A method of treating hair, the method comprising:
   a. contacting the hair with a mixture comprising:
     i. at least one ionic liquid comprising an imidazolium-based compound or ammonium-based compound,
     ii. at least one anionic surfactant, and
     iii. at least one first cationic direct dye,
     wherein the hair has been pre-dyed with a second cationic direct dye, and wherein the first and the second cationic direct dyes are the same or different.

12. The method of claim 11, wherein the ionic liquid comprises an imidazolium-based compound having a structure represented by Formula (I) below:

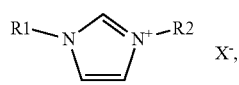

wherein
R1 and R2 are each independently selected from linear and branched alkyl groups having 1-16 carbon atoms, and
X is selected from halides, carboxylates, $C_{1-16}$ fatty acid carboxylates, phosphate, phosphate derivatives, tosylate, tosylate derivatives, sulfate, or sulfate derivatives.

13. The method of claim 12, wherein the ionic liquid comprises an imidazolium-based compound selected from 1-butyl-3-methylimidazolium octyl sulfate, 1-butyl-3-methylimidazolium acetate, 1-ethyl-3-methylimidazolium ethylsulfate, 1-ethyl-3-ethyl imidazolium acetate, 1-ethyl-3-methylimidazolium tosylate, or combinations thereof.

14. The method of claim 11, wherein the ionic liquid comprises an ammonium-based compound having a structure represented by Formula (II) below:

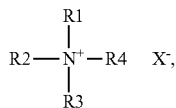

wherein R1, R2, R3, and R4 are each independently selected from saturated or unsaturated, linear, branched or cyclic groups with a carbon chain length of $C_{1-20}$, which are optionally substituted by one or more hydroxyl, amino $C_{1-4}$ radicals, alkylamino, carboxy, carboxylate, carbamide, $C_{1-4}$ alkoxy, $-SO_3H$, sulfonate or aryl; and X is selected from halides, carboxylates, $C_{1-16}$ fatty acid carboxylates, phosphate, phosphate derivatives, tosylate, tosylate derivatives, sulfate, or sulfate derivatives.

15. The method of claim 14, wherein the ionic liquid comprises an ammonium-based compound comprises tributylmethyl ammonium.

16. The method of claim 11, wherein the cationic dye is hydrophilic, and wherein the hydrophilic dye is selected from Basic Orange 31, Basic Red 51, Basic Yellow 87, Basic Red 76, or combinations thereof.

17. The method of claim 11, wherein the cationic dye has a negative log $P_{o/W}$ value, and wherein the cationic dye with negative log $P_{o/W}$ value is selected from Basic Orange 31, Basic Red 51, Basic Yellow 87, or combinations thereof.

18. The method of claim 11, wherein the anionic surfactant is selected from sodium laureth sulfate, alkyl sulfates including sodium lauryl sulfate, sodium dodecyl sulfate and ammonium lauryl sulfate, sulfosuccinates including disodium laureth sulfosuccinate, diethylhexyl sodium sulfosuccinates, dioctyl sodium sulfosuccinate, or combinations thereof.

19. The method of claim 11, wherein the first and second cationic direct dyes are the same.

* * * * *